(12) United States Patent
Bono et al.

(10) Patent No.: US 12,121,406 B2
(45) Date of Patent: *Oct. 22, 2024

(54) RETRACTABLE TOOL FOR ROBOTIC SURGERY

(71) Applicant: GLOBUS MEDICAL, INC., Audubon, PA (US)

(72) Inventors: Peter L Bono, Bingham Farms, MI (US); James D. Lark, West Bloomfield, MI (US); Thomas J. Lord, South Milwaukee, WI (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/474,578

(22) Filed: Sep. 26, 2023

(65) Prior Publication Data

US 2024/0065797 A1 Feb. 29, 2024

Related U.S. Application Data

(63) Continuation of application No. 16/879,447, filed on May 20, 2020, now Pat. No. 11,801,111.

(60) Provisional application No. 62/850,323, filed on May 20, 2019.

(51) Int. Cl.
*A61B 90/00* (2016.01)
*A61B 17/00* (2006.01)
*A61B 17/16* (2006.01)
*A61B 17/34* (2006.01)
*A61B 34/30* (2016.01)
*A61B 90/50* (2016.01)

(52) U.S. Cl.
CPC .............. *A61B 90/08* (2016.02); *A61B 17/16* (2013.01); *A61B 34/30* (2016.02); *A61B 2017/00477* (2013.01); *A61B 2017/00544* (2013.01); *A61B 2017/1602* (2013.01); *A61B 17/34* (2013.01); *A61B 2090/08021* (2016.02); *A61B 90/50* (2016.02)

(58) Field of Classification Search
CPC ......... A61B 90/08; A61B 34/30; A61B 17/16; A61B 2090/08021; A61B 90/50; A61B 17/34; A61B 2017/00477; A61B 2017/00544; A61B 2017/1602
See application file for complete search history.

(56) References Cited

FOREIGN PATENT DOCUMENTS

EP 3064162 A2 9/2016
WO WO-2013018932 A1 * 2/2013 .............. A61B 17/29

* cited by examiner

*Primary Examiner* — Zade Coley
*Assistant Examiner* — Diana Jones

(57) ABSTRACT

The invention involves a system and method for quickly retracting a tool from a surgical site. The system is generally constructed and arranged for attachment to a robotic arm for manipulation of the tool to perform an in-vivo surgery. The tool is constructed to retract from the surgical site upon a predetermined condition. The system and the robot can be reset when the condition has cleared so that the surgery can continue.

20 Claims, 25 Drawing Sheets

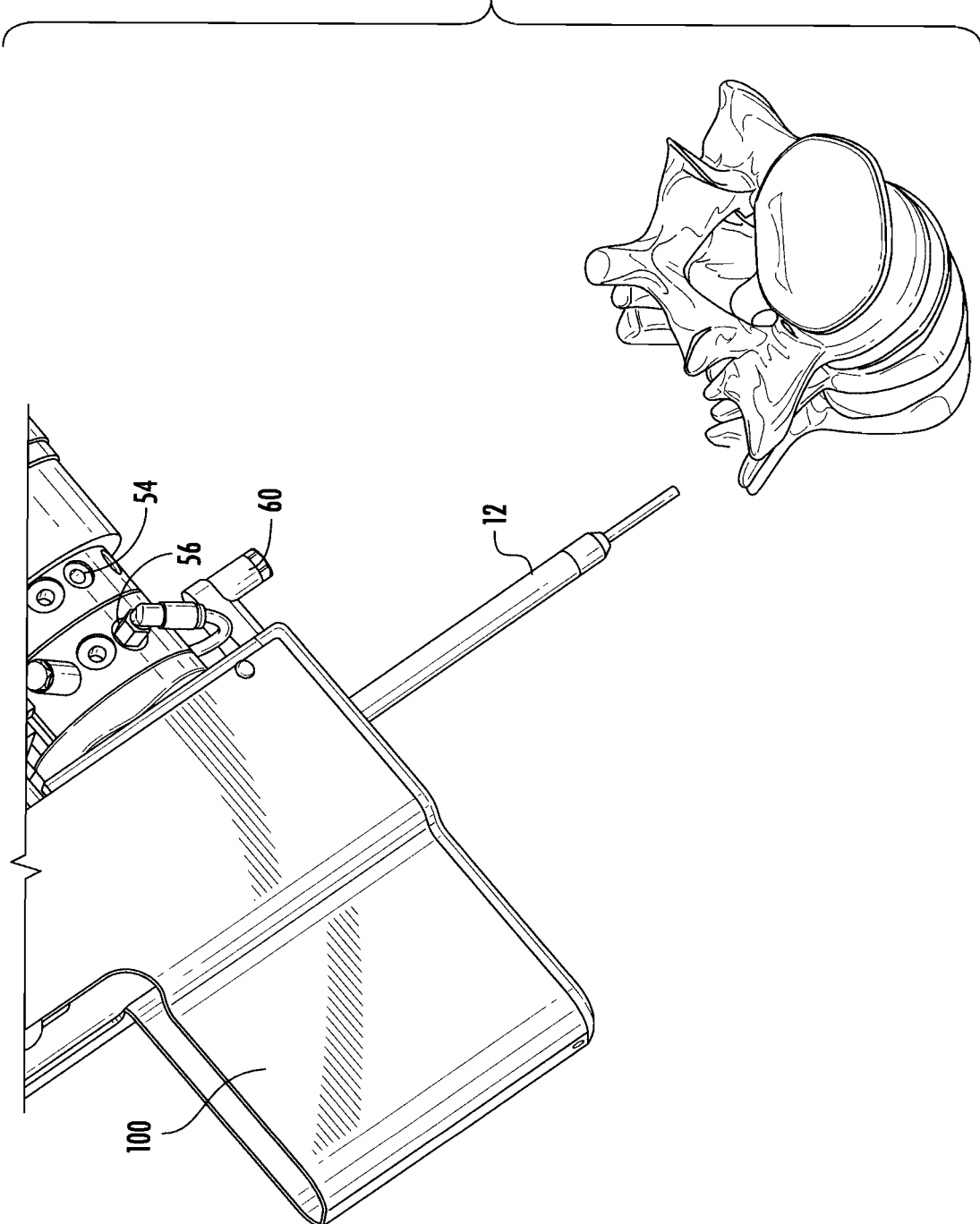

RETRACTABLE TOOL FOR ROBOTIC SURGERY

RELATED APPLICATIONS

In accordance with 37 C.F.R 1.76, a claim of priority is included in an Application Data Sheet filed concurrently herewith. Accordingly, under 35 U.S.C. § 119(e), 120, 121, and/or 365(c), the present invention is a continuation application of U.S. patent application Ser. No. 16/879,447, filed on May 20, 2020 (published as U.S. Pat. Pub. No. 2020-0367989), which claims priority of U.S. Patent Application No. 62/850,323, entitled "RETRACTING TOOL FOR ROBOTIC SURGERY," filed on May 20, 2019. The contents of the above referenced applications are herein incorporated by reference in its entirety for all purposes.

FIELD OF INVENTION

The present invention generally relates to robotic surgery and, more particularly, to a tool constructed to retract from the surgical site upon a predetermined condition.

BACKGROUND INFORMATION

Robotic surgery, computer-assisted surgery, and robotically-assisted surgery are terms for technological developments that use robotic systems to aid in surgical procedures. Robotically-assisted surgery was developed to overcome the limitations of pre-existing minimally-invasive surgical procedures and to enhance the capabilities of surgeons performing open surgery.

In the case of robotically-assisted minimally-invasive surgery, instead of directly moving the instruments, the surgeon uses one of two methods to control the instruments; either a direct telemanipulator or through computer control. A telemanipulator is a remote manipulator that allows the surgeon to perform the normal movements associated with the surgery while the robotic arms carry out those movements using end-effectors and manipulators to perform the actual surgery on the patient. In computer-controlled systems, the surgeon uses a computer to control the robotic arms and its end-effectors, though these systems can also still use telemanipulators for their input. One advantage of using the computerized method is that the surgeon does not have to be present, but can be anywhere in the world, leading to the possibility for remote surgery. One drawback of these systems relates to interference in the sensors that monitor the location of the robotic components, including the tools being used by the robot to complete the surgery. Surgical tools, and even robotic components, are often constructed from materials that are not radio translucent, and thus they cause interference with the sensors used to guide the robot to its desired precise location. The interference may cause the robot to not be located where it should be, and may cause problems with the surgery.

In the case of enhanced open surgery, autonomous instruments (in familiar configurations) replace traditional surgical tools, performing certain actions (such as rib spreading) with much smoother, feedback-controlled motions than could be achieved by a human hand. The main object of such smart instruments is to reduce or eliminate the tissue trauma traditionally associated with open surgery. This approach seeks to improve open surgeries, particularly orthopedic, that have so far not benefited from robotic techniques by providing a tool that can provide a quick retraction of the tool from the surgical site should a need arise for something, such as a patient cough or patient movement, power outages, or other threatening circumstances.

One major drawback to utilizing robots for surgical procedures is their vulnerability to movement by the patient. These movements can lead to incorrect position and orientation reporting.

Another drawback relates to power outages or electrical interference that causes the robot positional confusion or loss.

There exists, therefore, a need for a robotic system that is capable of reducing or eliminating problems occurring from patient movements to provide safer robotic surgery.

Thus, the present invention provides a system and method for providing a fast tool retraction for robotic or robotic assisted surgeries. The system is constructed to quickly retract the surgical tool from the surgical site. The tool retractor system and the robot can be reset to complete the surgery once the error has been corrected.

SUMMARY OF THE INVENTION

Briefly, the invention involves a system and method for increasing positional accuracy and safety of surgical systems that utilize a robot for performance of surgery. The system allows cutting tools to be quickly retracted from the surgical site upon detection of patient movement or some other issue that could result in positional inaccuracy for the robot. The system can be reset once the error has been cleared, and the position with respect to the patient re-established.

Accordingly, it is an objective of the present invention to provide a method and system for retracting cutting tools from a surgical site in a rapid manner.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

BRIEF DESCRIPTION OF THE FIGURES

FIG. 25 is a partial perspective view of the embodiment shown in FIG. 22, illustrating the cutting tool in a retracted position.

DETAILED DESCRIPTION OF THE PREFERRED EMBODIMENTS

Figure 1:
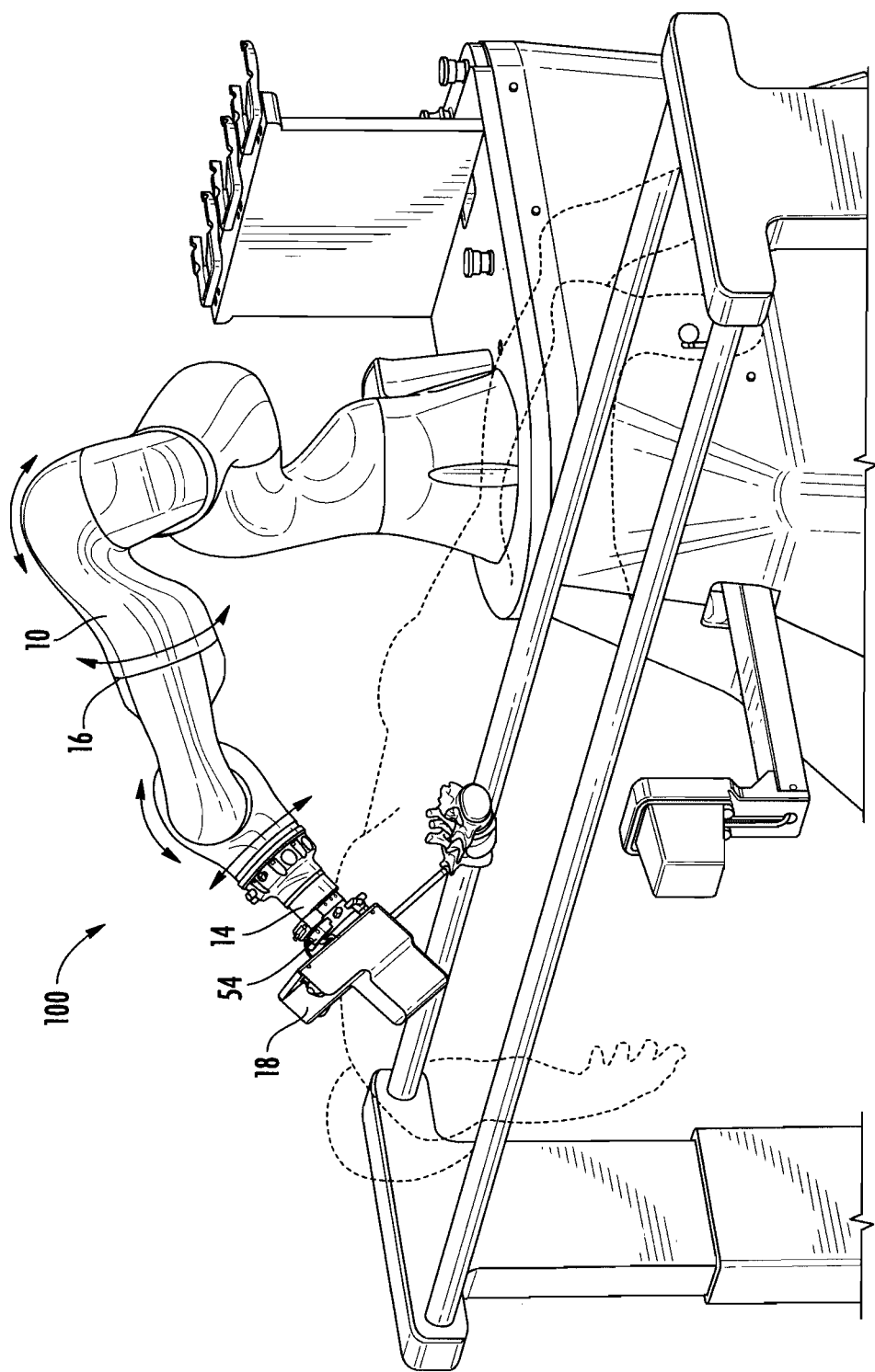
FIG. 1 is a top front perspective view of one embodiment of the present invention.
Figure 2:
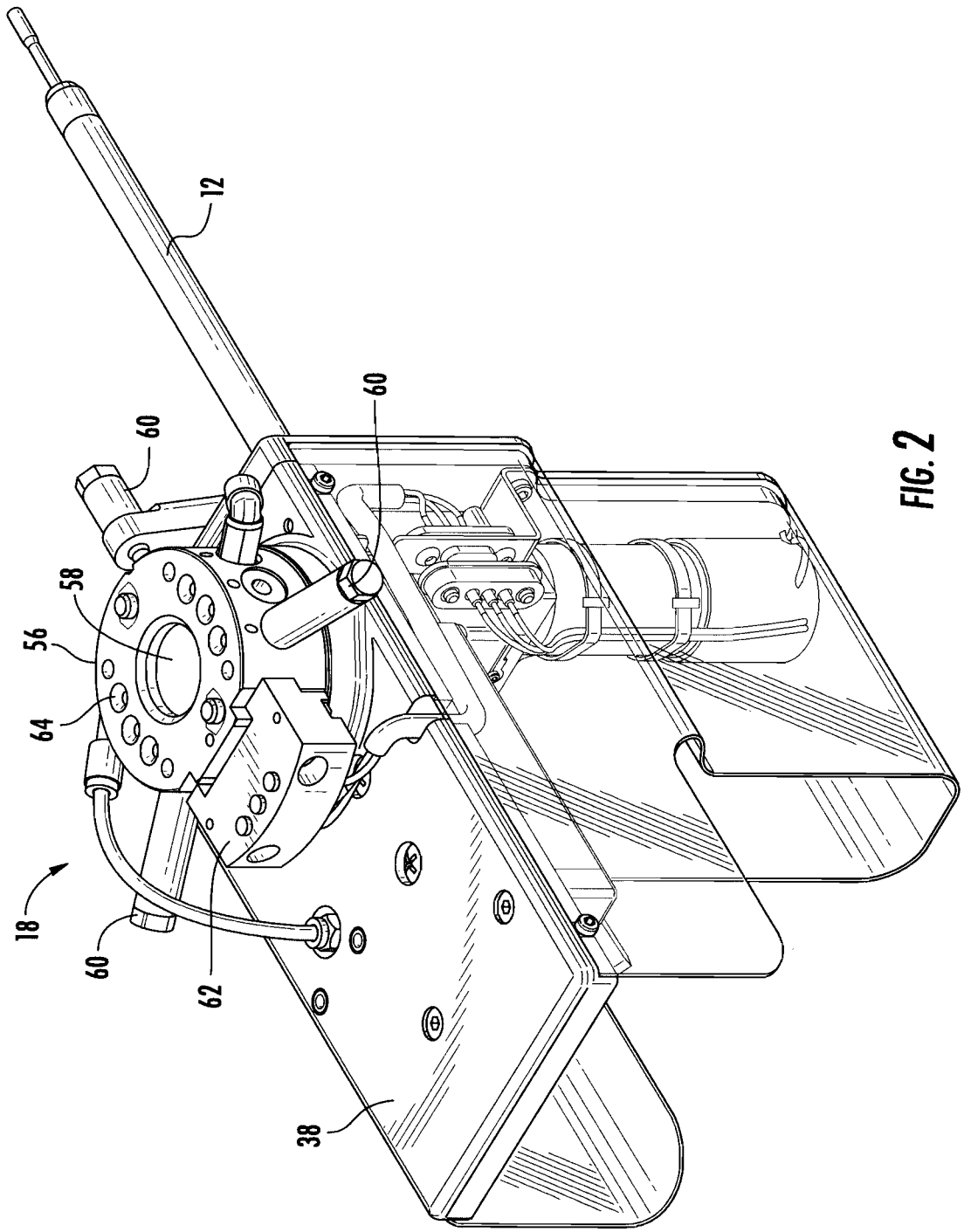
FIG. 2 is a partial top perspective view of the embodiment shown in FIG. 1, illustrating one embodiment of the retraction mechanism.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Figure 3:
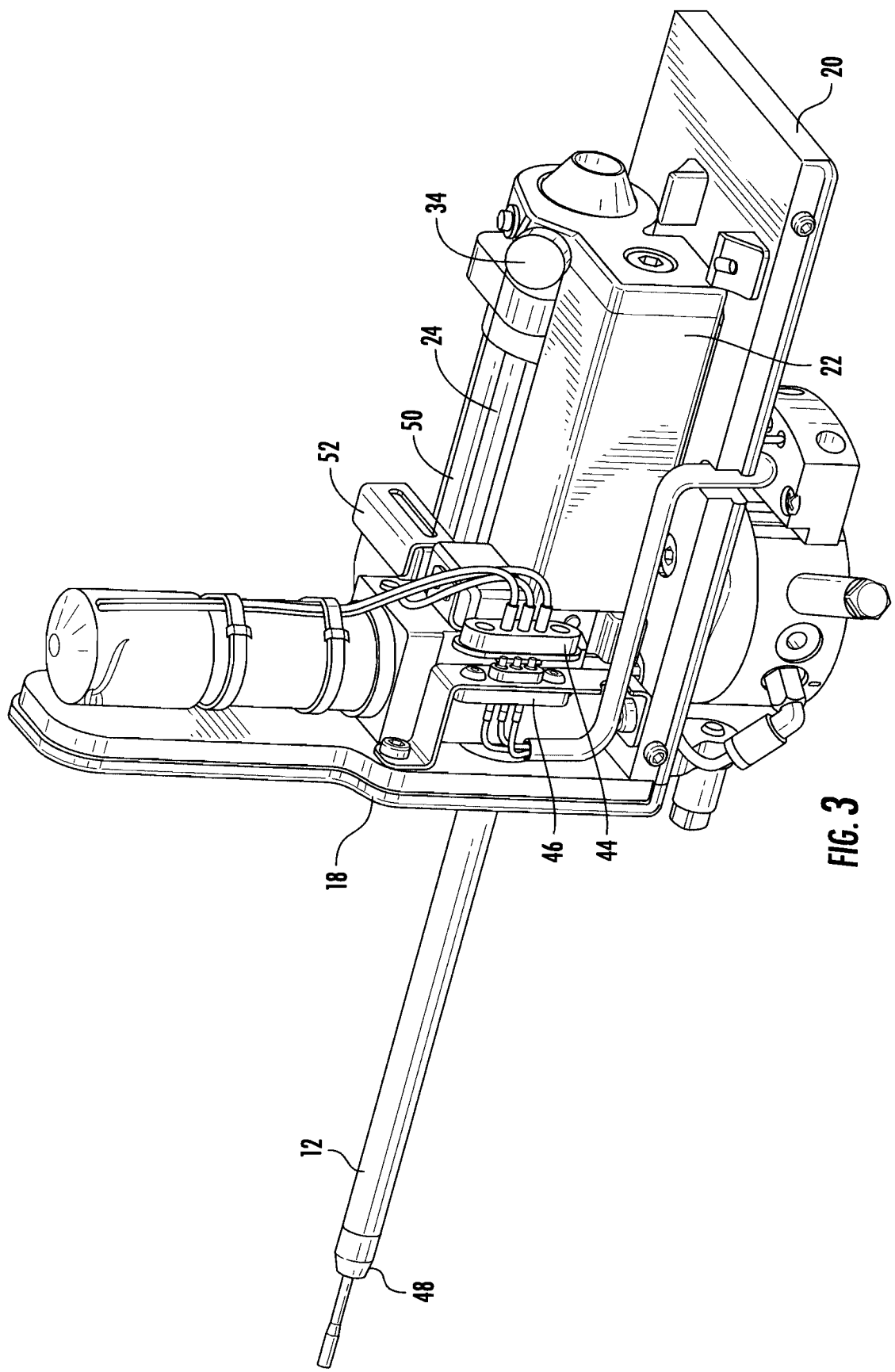
FIG. 3 is a partial bottom perspective view of the embodiment shown in FIG. 2.
Figure 4:
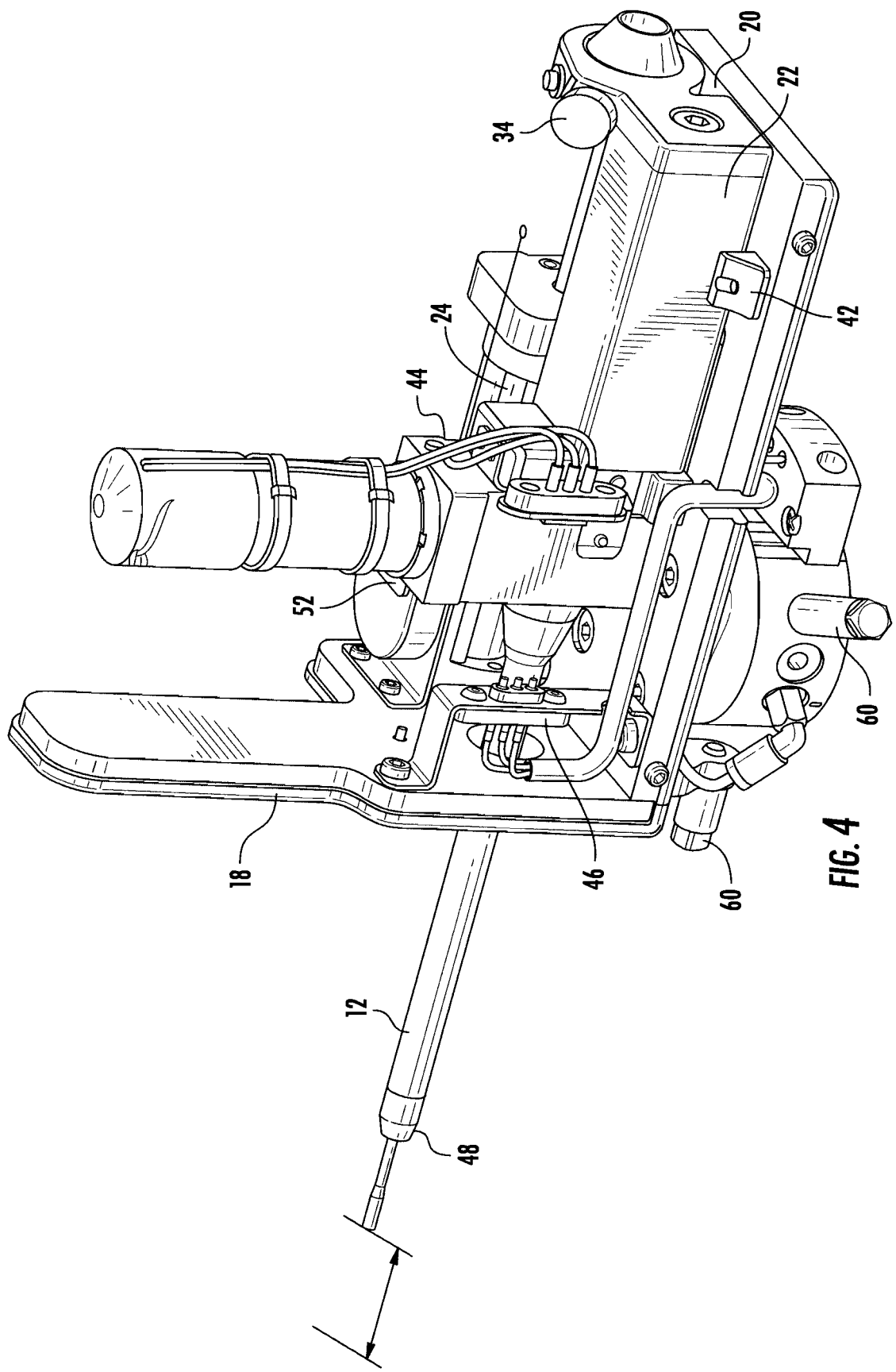
FIG. 4 is a partial perspective view of the embodiment shown in FIG. 2, illustrating the tool in a retracted position.
Figure 5:
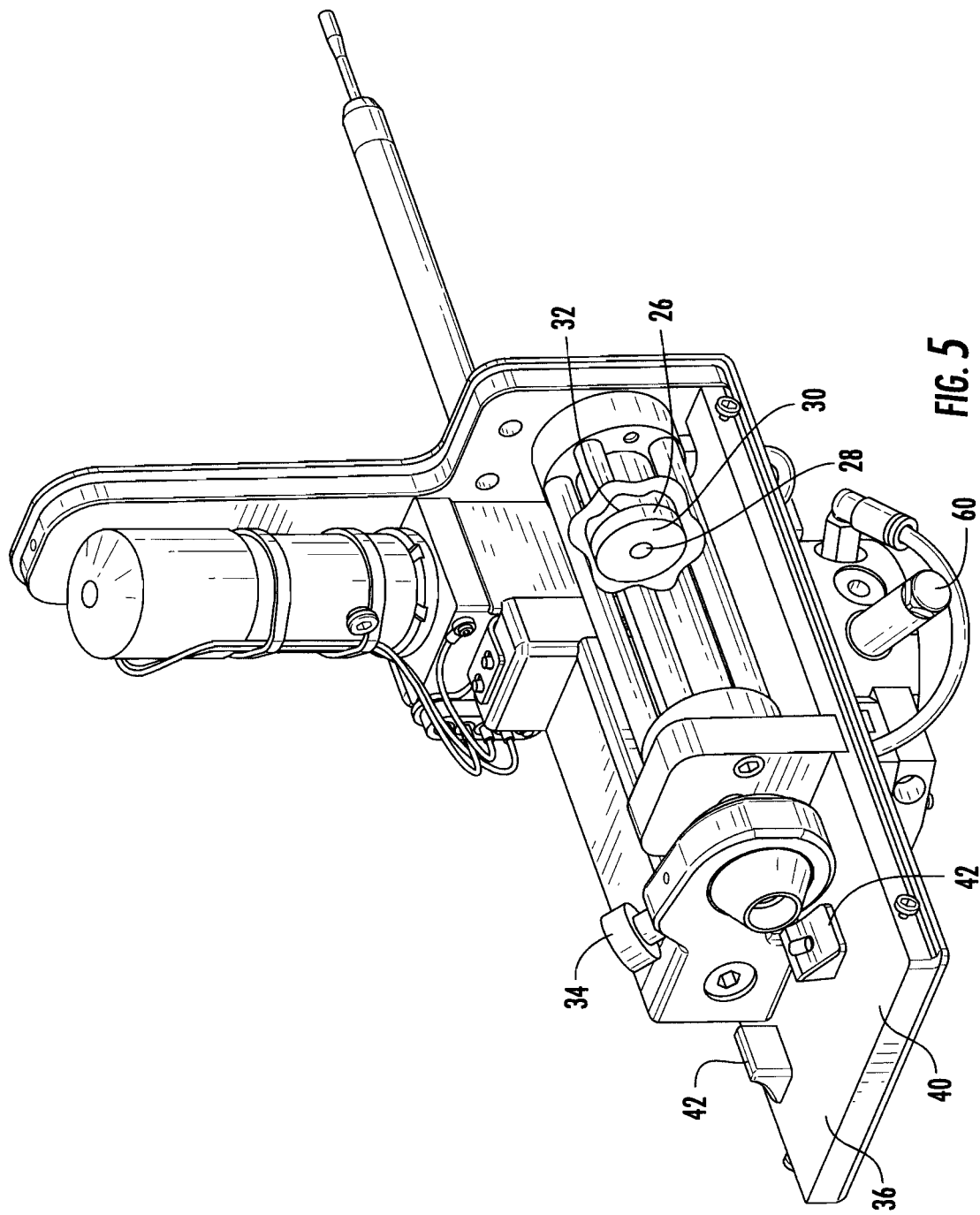
FIG. 5 is a partial perspective view of the embodiment shown in FIG. 2, illustrating the internal components of one embodiment of the present device and system.
Figure 6:
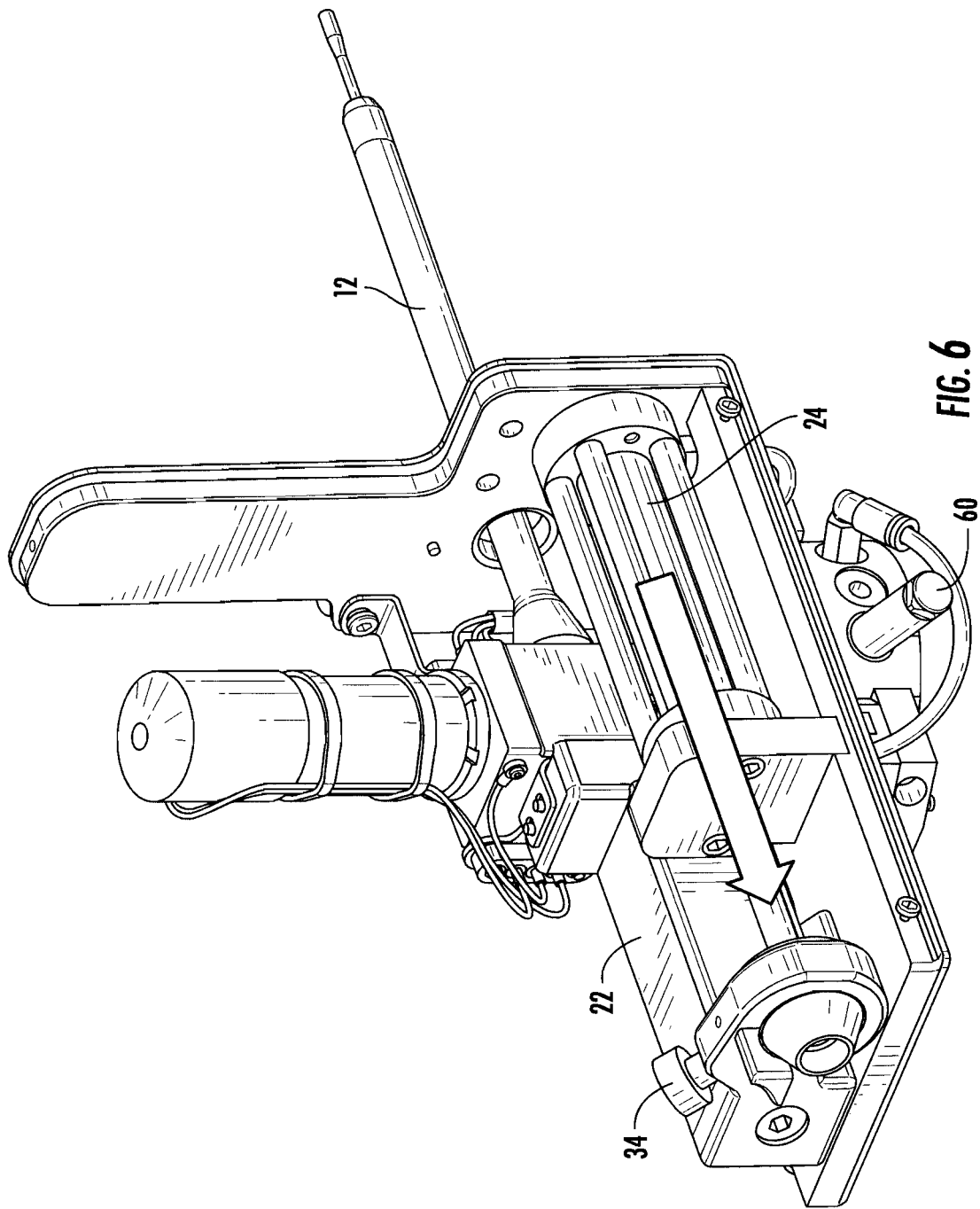
FIG. 6 is a partial perspective view of the embodiment shown in FIG. 5, illustrating the internal components in a retracted position.
Figure 7:
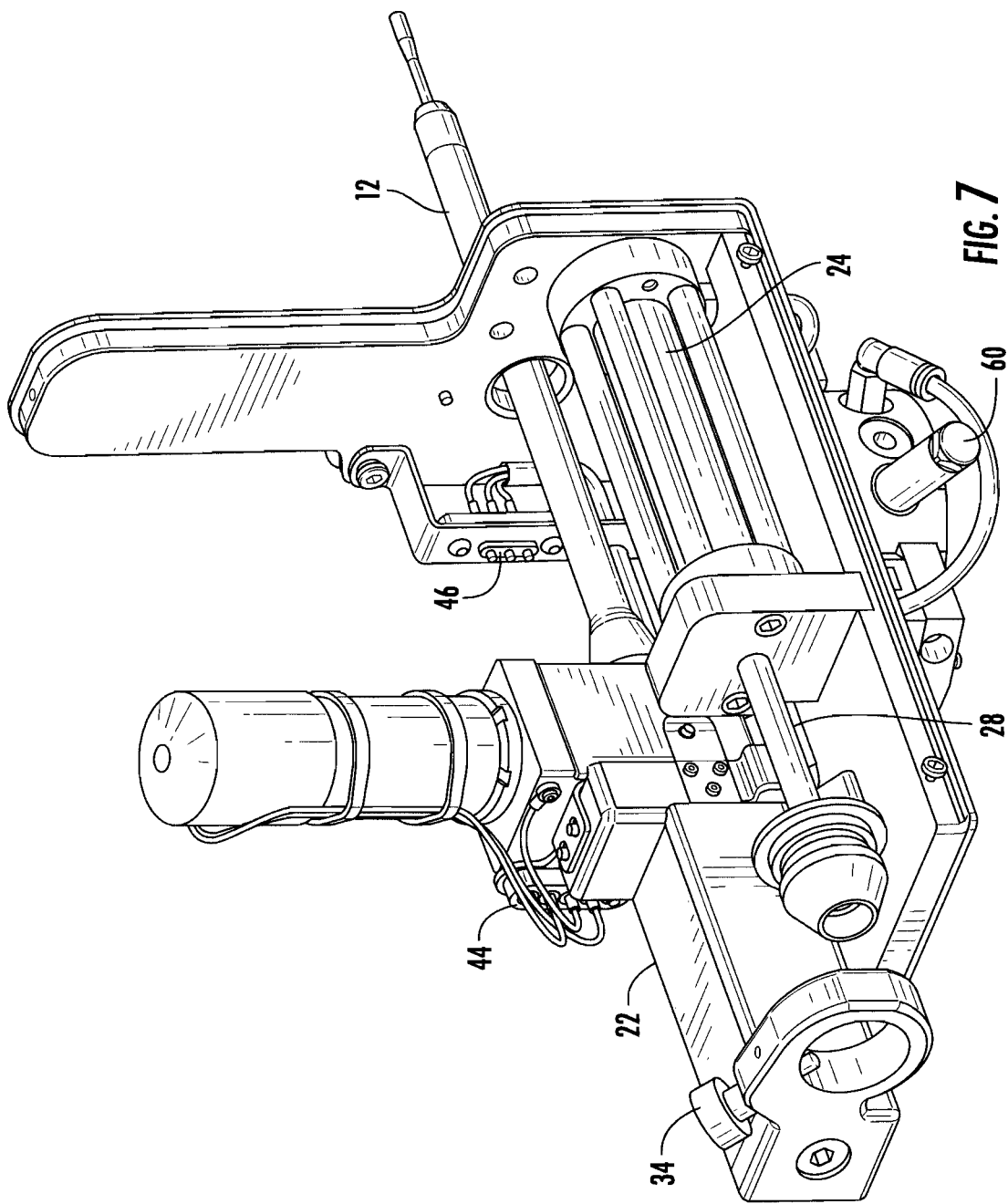
FIG. 7 is a partial perspective view of the embodiment shown in FIG. 5, illustrating further retraction of the tool.
Figure 8:
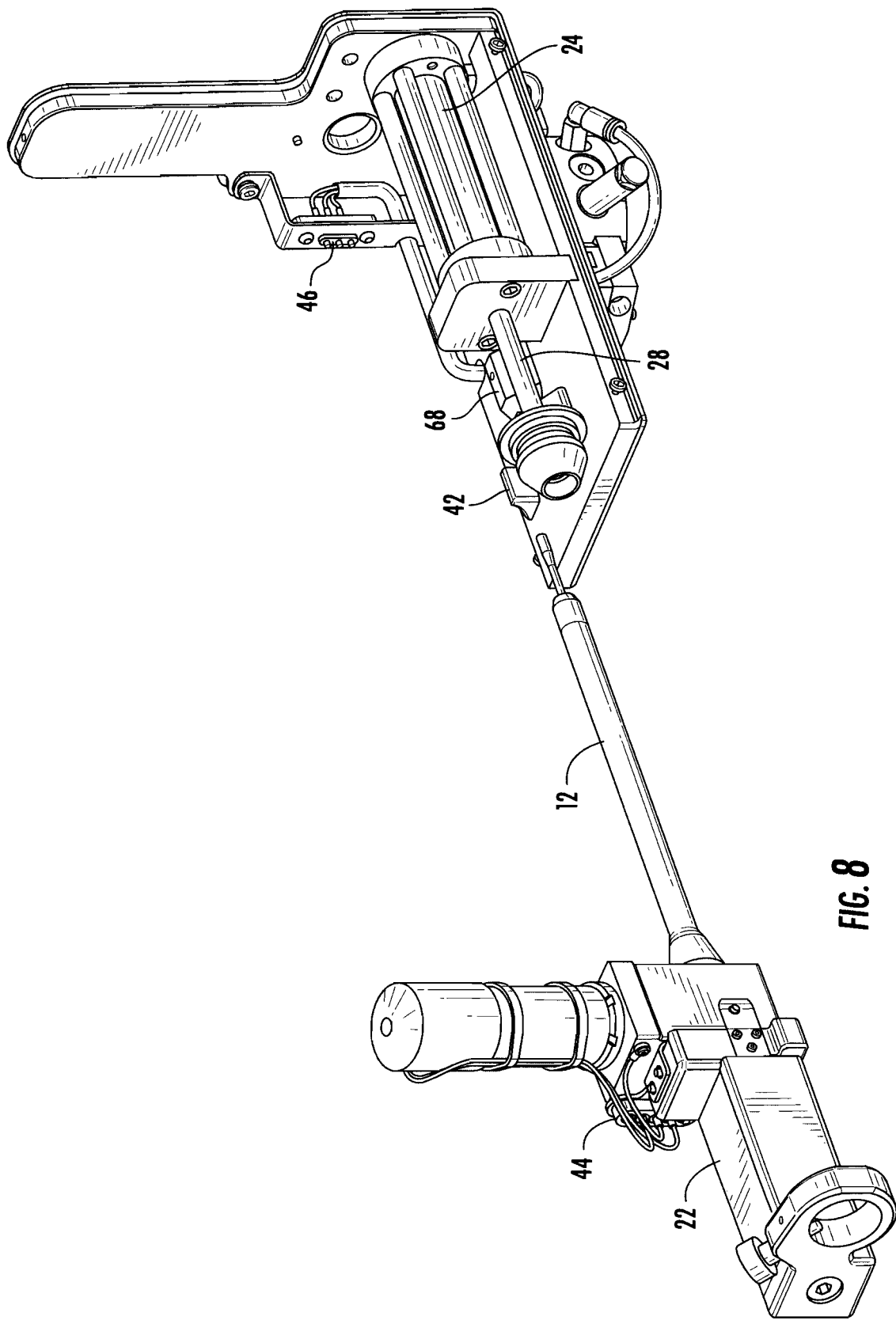
FIG. 8 is a partial perspective view of the embodiment shown in FIG. 5, illustrating removal of the tool.
Figure 9A:
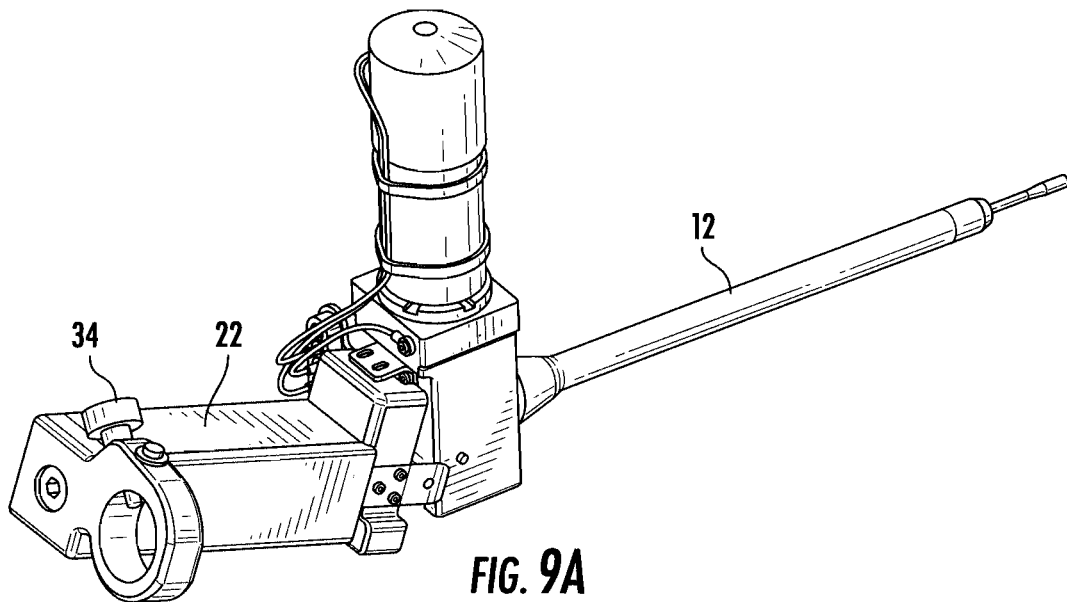
FIG. 9A is a partial side view illustrating replacement of the cutting tool.
Figure 9B:
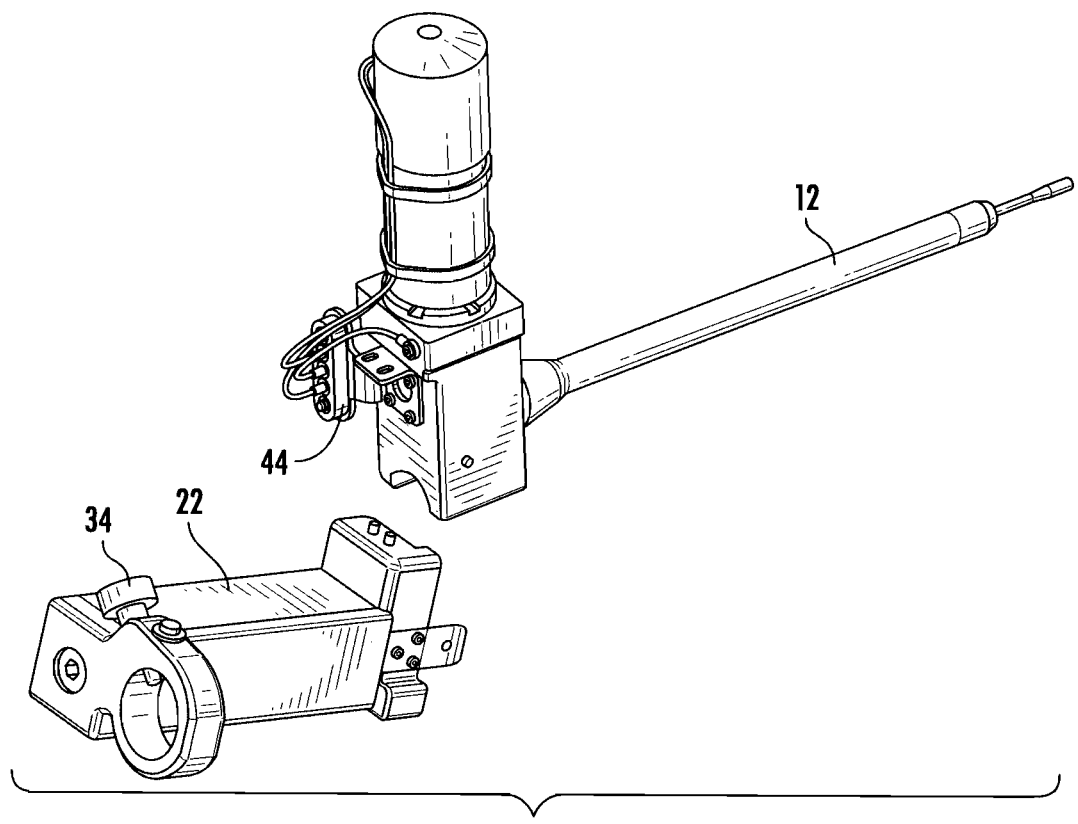
FIG. 9B is a partial side view illustrating replacement of the cutting tool.
Figure 10:
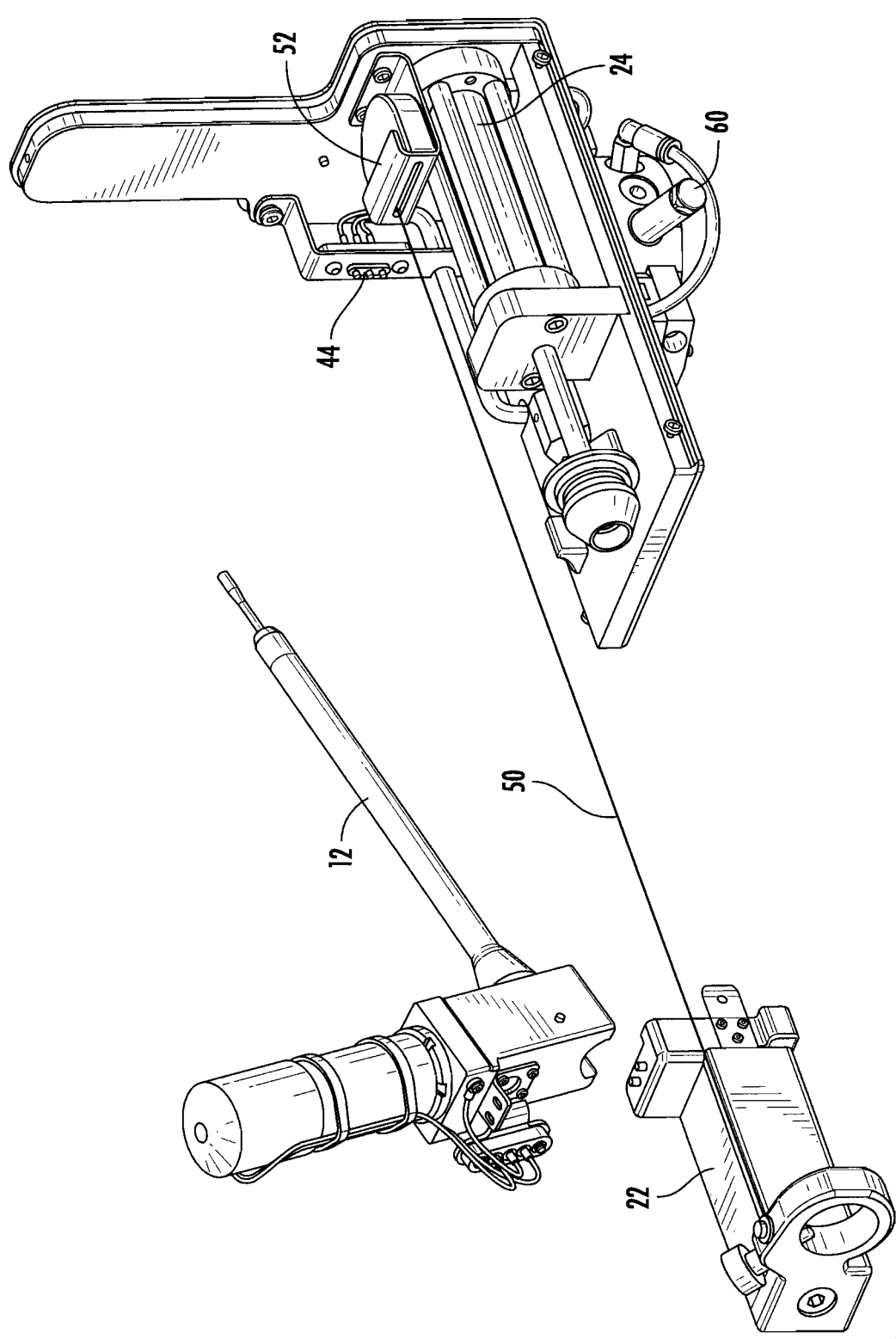
FIG. 10 is a partial perspective view illustrating removal and replacement of the cutting tool.

Referring generally to FIGS. 1-25, a system and method for quickly retracting a tool from a surgical site is illustrated. The retraction system 100 is generally constructed and arranged for attachment to a robotic arm 10 for manipulation of the surgical tool 12 to perform an in-vivo surgery. The retraction system 100 is constructed to retract at least a portion of the surgical tool 12 from the surgical site upon a predetermined condition. The retraction system 100 and the robot arm 10 can be reset when the condition has cleared so that the surgery can continue. The robotic arm 10 includes at least one axis of movement, and the most preferred embodiment includes six or seven axes of movement for manipulation of the surgical tool. The robotic arm 10 includes an attachment point 14 for securing a tool 12 to the robot for robotically controlled movement of the tool for completion of at least a portion of a surgical procedure. In a preferred embodiment, the surgical tool includes a retraction mechanism 18 for causing said surgical tool 12 to retract from a first operational position (FIG. 3) to a second non-operational position (FIG. 4) independent of the robotically controlled movement of the tool upon detection of a predetermined condition. Such predetermined conditions may include, but should not be limited to, movement of the patient as monitored by a camera or electromagnetic system, patient cough, patient, power fluctuation or outage, etc.

Still referring to FIGS. 1-25, the retraction mechanism 18 preferably includes a track portion 20 and a shuttle portion 22. A functional portion of the surgical tool 12 is secured to the shuttle portion 22 to move therewith upon detection of one of the predetermined conditions so that movement of the shuttle portion 22 disables movement of the functional portion of said tool. For example, if the tool is a rotary tool, such as a grinder or drill, rotation of the grinder or drill would be disabled. In the case of a tool, such as a Jamshidi needle, the needle would be sufficiently retracted to remove the needle from the surgical site. Likewise, other surgical tools would either be disabled from movement used to modify tissue and/or be retracted from the surgical site, thereby preventing the tool from causing damage to tissue surrounding the surgical site, i.e. disabling the functional portion of the surgical tool. In a most preferred embodiment, disablement would include, but would not be limited to, removal of motive power to the functional portion of the surgical tool.

Still referring to FIGS. 1-25, in at least one embodiment, movement of the shuttle 22 is provided by a second source of motive power, which may be pneumatic and in the form of vacuum or pressure without departing from the scope of the invention. The pneumatic motive power may be fluidly connected to an air cylinder 24 having a moveable piston 26 therein. The pneumatic motive power is supplied to a first side 30 of said piston 26 to position said surgical tool 12 in the operational position, and whereby supplying the pneumatic motive power to the second side 32 of the piston 26 causes the surgical tool 12 to retract to the non-operational position. It should be noted that the aforementioned orientation of pneumatic motive power is assuming pressurized fluid; those skilled in the art will readily recognize that should vacuum be the pneumatic motive power that the side of the piston to which the pneumatic power is provided to cause the desired movement will be reversed. In a preferred embodiment, the first side 30 of the piston 26 includes a rod member 28 secured thereto. The rod member 28 extends through an end portion of the air cylinder and moves with the piston 26. The rod 28 is connected to the shuttle 22 so that the shuttle 22 moves with the piston 26. In at least one embodiment, the shuttle 22 is removably secured to the rod 28, whereby the surgical tool or the operative portion of the surgical tool 12 is removable and replaceable with respect to the shuttle 22. To facilitate the removal and replacement of the surgical tool, a hand operated spring pin 34 may be utilized. Fasteners or the like may be substituted for the spring pin without departing from the scope of the invention. It should be noted that while the cylinder is illustrated as including the rod member 28, magnetic coupling of the piston 26 to the shuttle 22 may be utilized without departing from the scope of the invention. Such construction of pneumatic cylinders is commonly referred to as linear motors in the industrial arts. It should also be noted that, in the preferred embodiment, the cylinder is constructed and arranged to move the surgical tool 12 about one and one half inches or about 38 millimeters, and the movement occurs in a fraction of a second.

Figure 19:
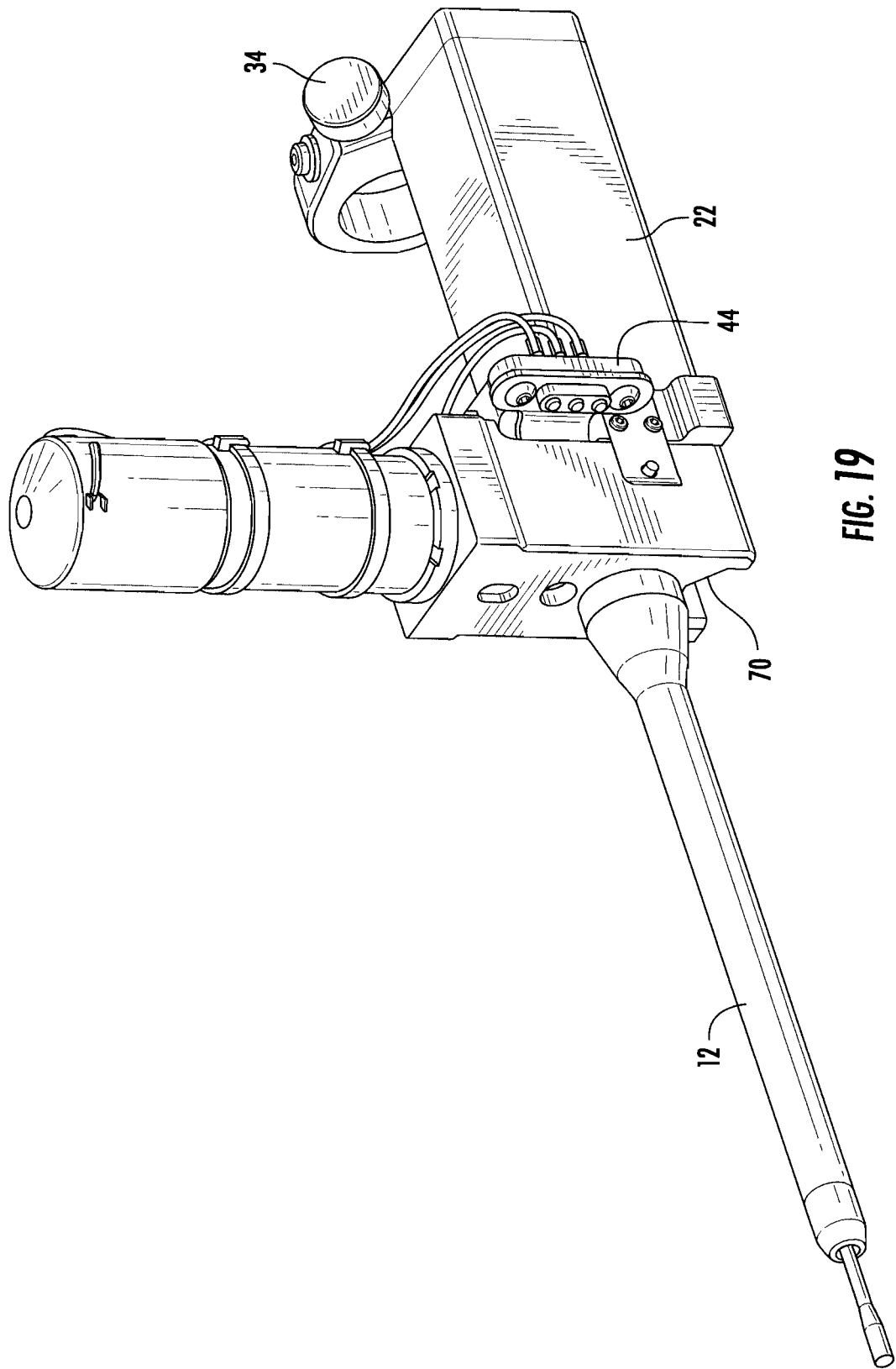
FIG. 19 is a perspective view illustrating the cutting tool.
Figure 20:
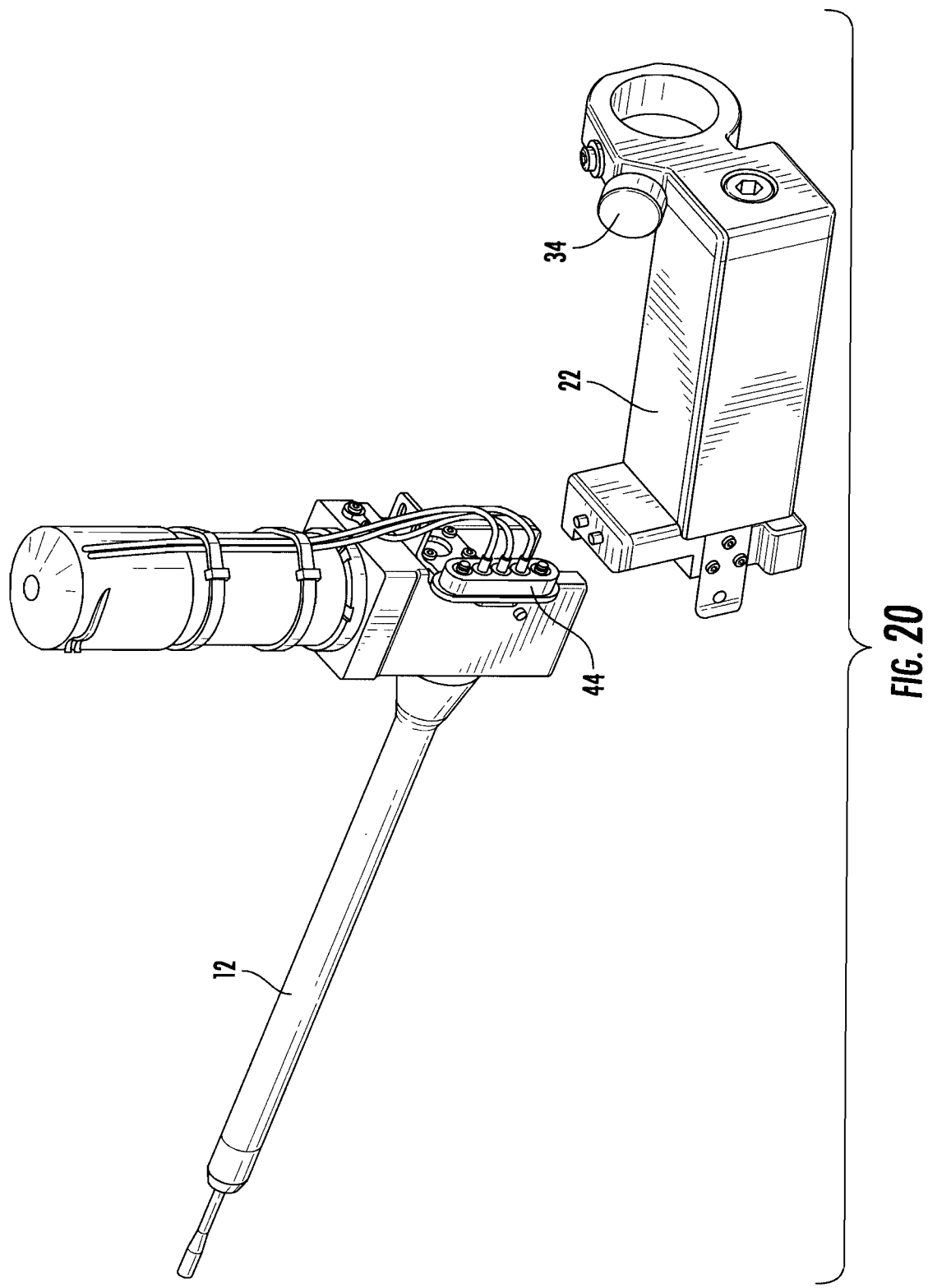
FIG. 20 is a perspective view illustrating separation of the cutting tool from a portion of the retraction mechanism.
Figure 21:
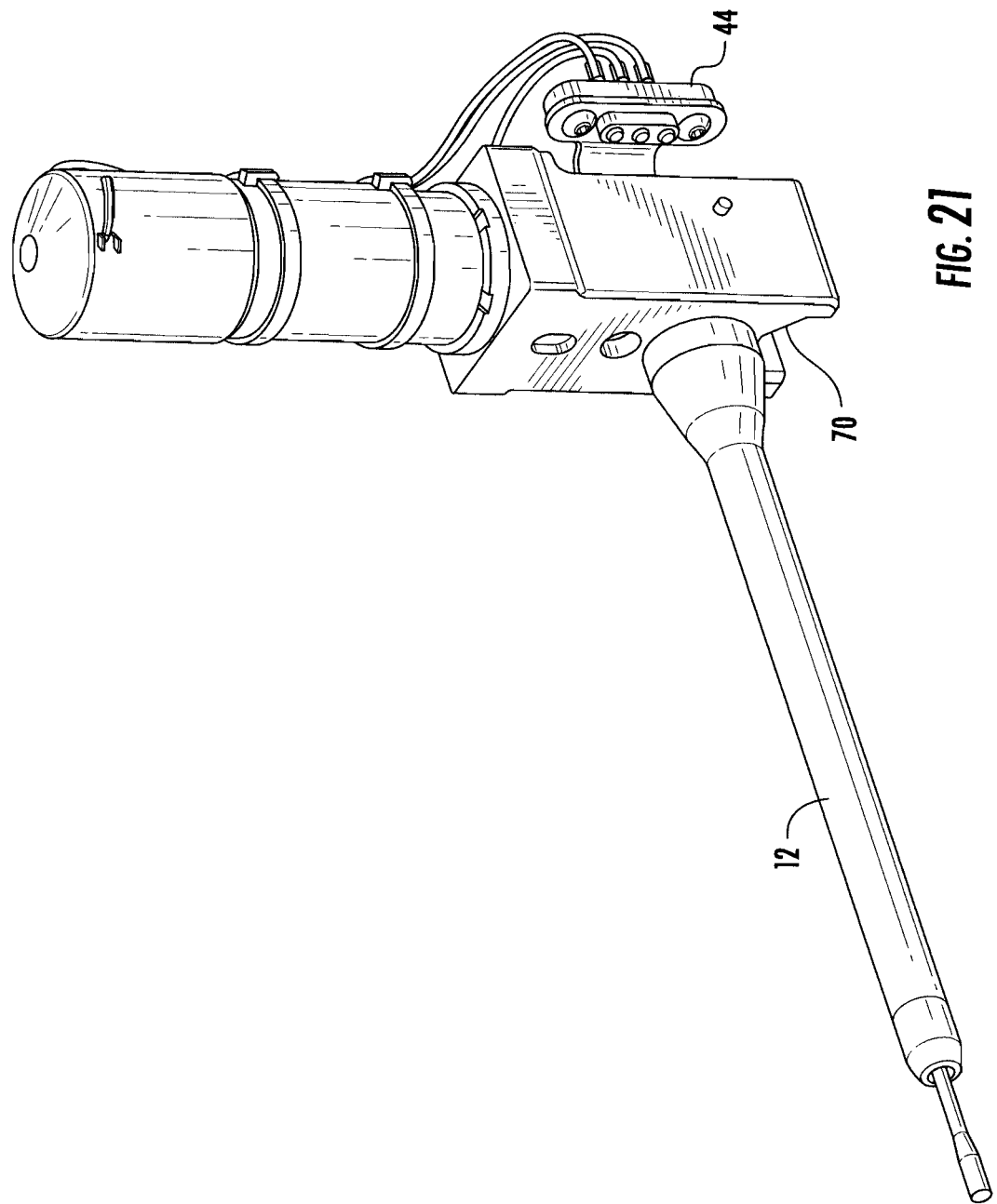
FIG. 21 is a perspective view of the cutting tool, in this embodiment a rotary burr.
Figure 22:
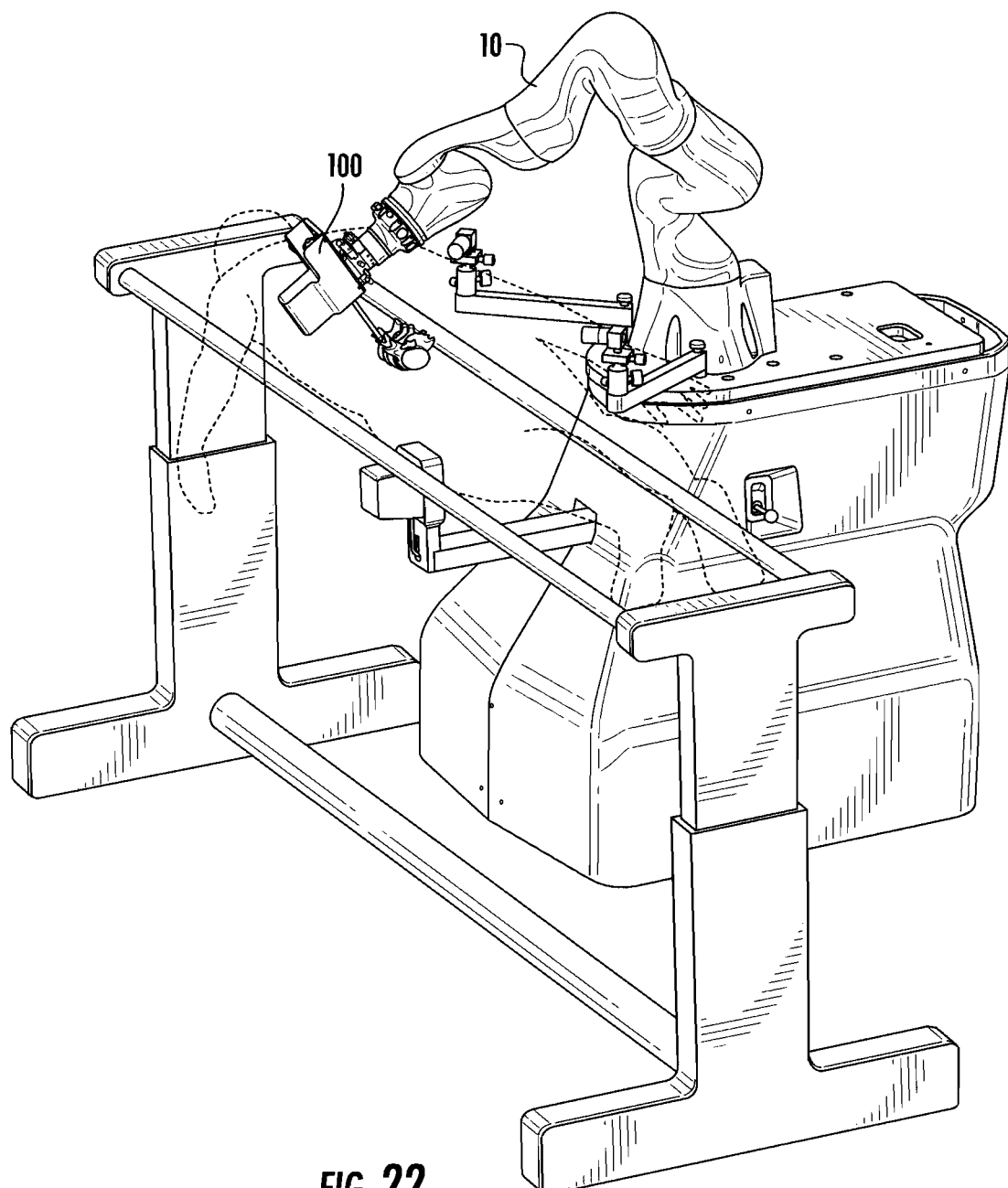
FIG. 22 is a perspective view of the retraction assembly in cooperation with a multi-axes automotive style robot preforming an in-vivo surgery.
Figure 23:
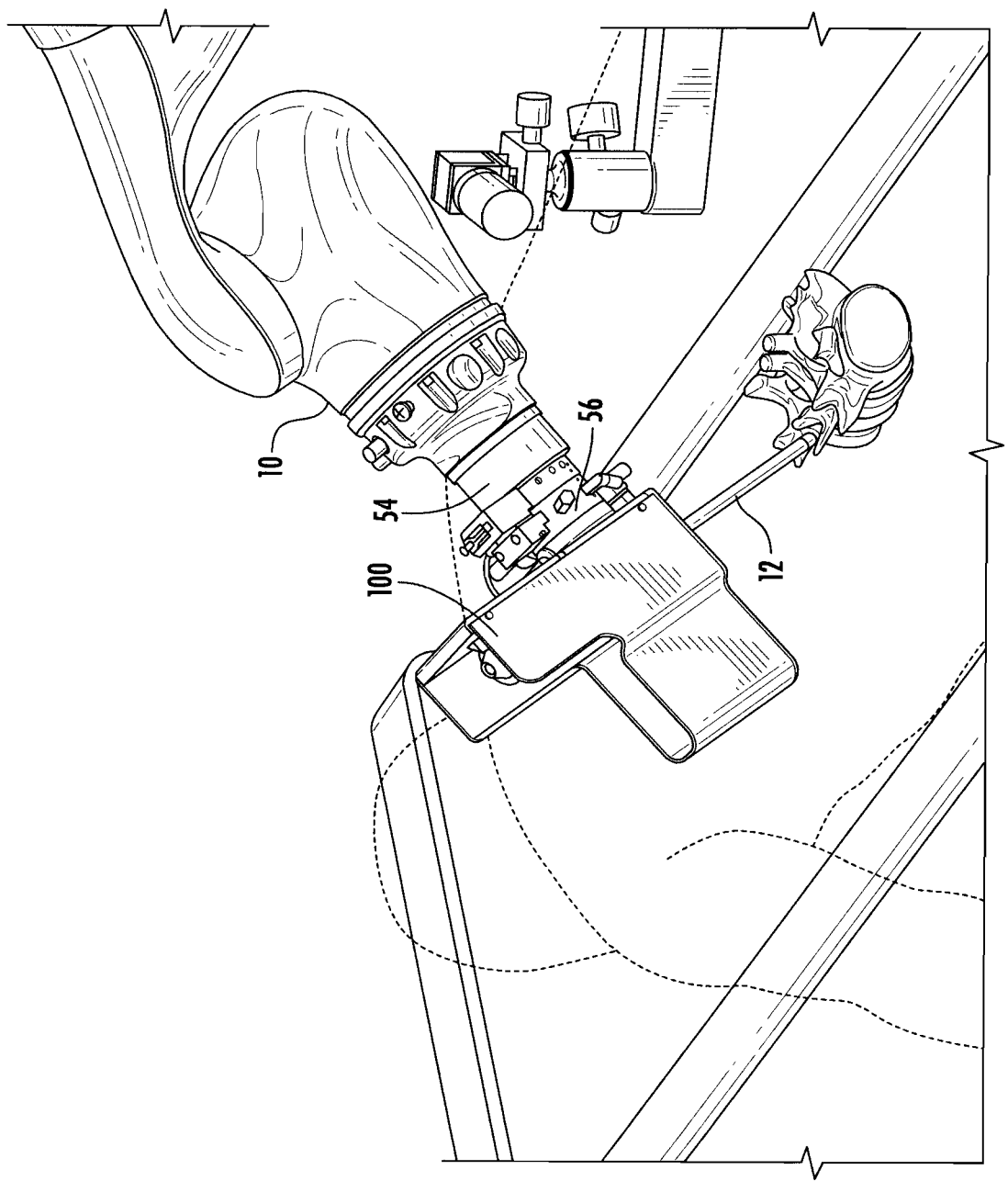
FIG. 23 is a partial perspective view of the embodiment shown in FIG. 22, illustrating the cutting tool working on a spine.
Figure 24:
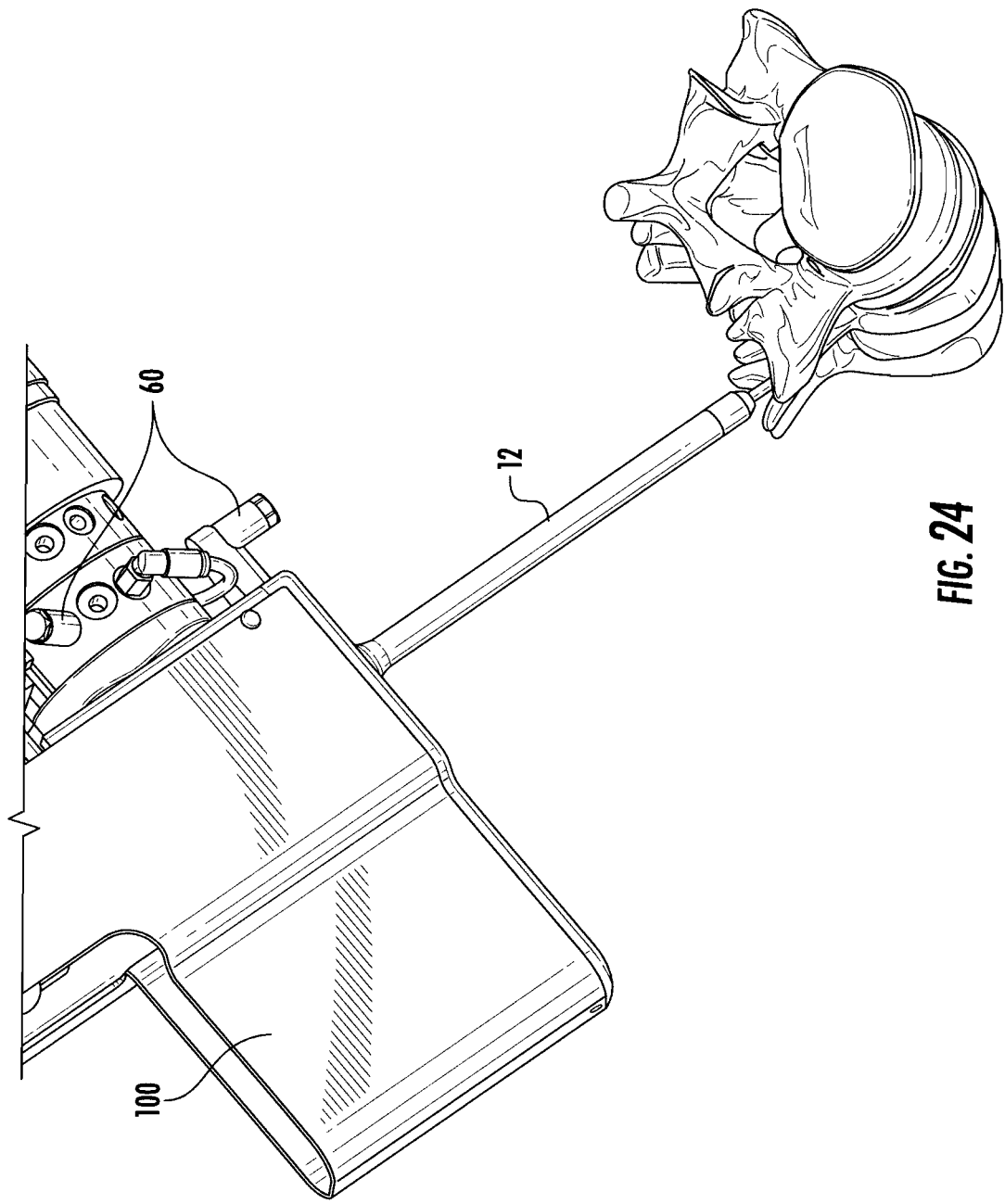
FIG. 24 is a partial perspective view of the embodiment shown in FIG. 22, illustrating the cutting tool working on a spine.

Still referring to FIGS. 1-25, the track portion 20 includes a plate 36, the plate 36 having a first side surface 38 and a second side surface 40. The first side surface 38 is secured to the robot attachment point 14, while the second side surface 40 includes the track portion 20. In one embodiment, the track portion 20 includes at least two guide members 42 for guiding the shuttle 22 during movement thereof between the operational position and the non-operational position. Some embodiments are provided with a male dove tail 68 (FIG. 8) which slidably cooperates with a conjugatedly shaped female dove tail 70. (FIG. 19). The dove tails interlock to prevent side to side and up and down movements while allowing guided sliding movement. The cooperating dove tails 68, 70 also allow the surgical tool to be accurately positioned and repositioned after the tool has been retracted. The shuttle 22 preferably includes at least one first set of electrical contacts 44, while the track portion includes at least one second set of electrical contacts 46. The first set of electrical contacts 44 and the second set of electrical contacts 46 are positioned to contact each other when the shuttle 22 is positioned in the operational position, and thus provide electrical flow to said surgical tool 12 for operation thereof. In this manner, the first set of electrical contacts 44 and the second set of electrical contacts 46 are separated during movement of the shuttle to the non-operational position, thereby disabling electrical motive movement of the surgical tool 12. In at least one embodiment, the surgical tool may be a rotary drill or grinder 48. Thus, all or portions of the drill/grinder are subject to wear and may need to be replaced periodically. Therefore, the drill/grinder 48 may be removably secured to the shuttle 22 and a reusable portion of the shuttle may be tethered to the plate 36 with a flexible member 50 such as a cable. A retractor mechanism 52 may be provided to allow the shuttle to be moved further away from the plate. Upon replacement of any necessary parts, the shuttle 22 may simply be snapped back together and the spring pin utilized to connect the shuttle 22 to the cylinder rod 28.

Still referring to FIGS. 1-25, the first side surface 38 of the plate 36 includes a tool change structure 56 for interlocking cooperation with a tool change mechanism 54. The tool change mechanism 54 is secured to the robot arm 10 to provide for tool interchangeability to the robot. Therefore, each surgical tool 12 is preferably a self-contained system connectable to the tool change mechanism 54, which provides the first motive power and the second motive power to the tool retraction system 100 through the tool change structure 56. In the preferred embodiment, the tool change structure 56 includes a pilot aperture 58 for providing positional location of said tool with respect to robot arm 10. A plurality of rod members 60 are secured about a periphery of the pilot aperture 58 for providing orientation of the surgical tool 12 with respect to the robot arm 10. Positioned between the rod members 60 is at least one primary electrical contact 62 for supplying electrical motive power to the surgical tool 12 for operation thereof. Also provided as part of the tool change structure 56 and mechanism 54 is at least one primary pneumatic connection 64 for supplying pneumatic motive power to the cylinder for operation thereof.

Figure 11:
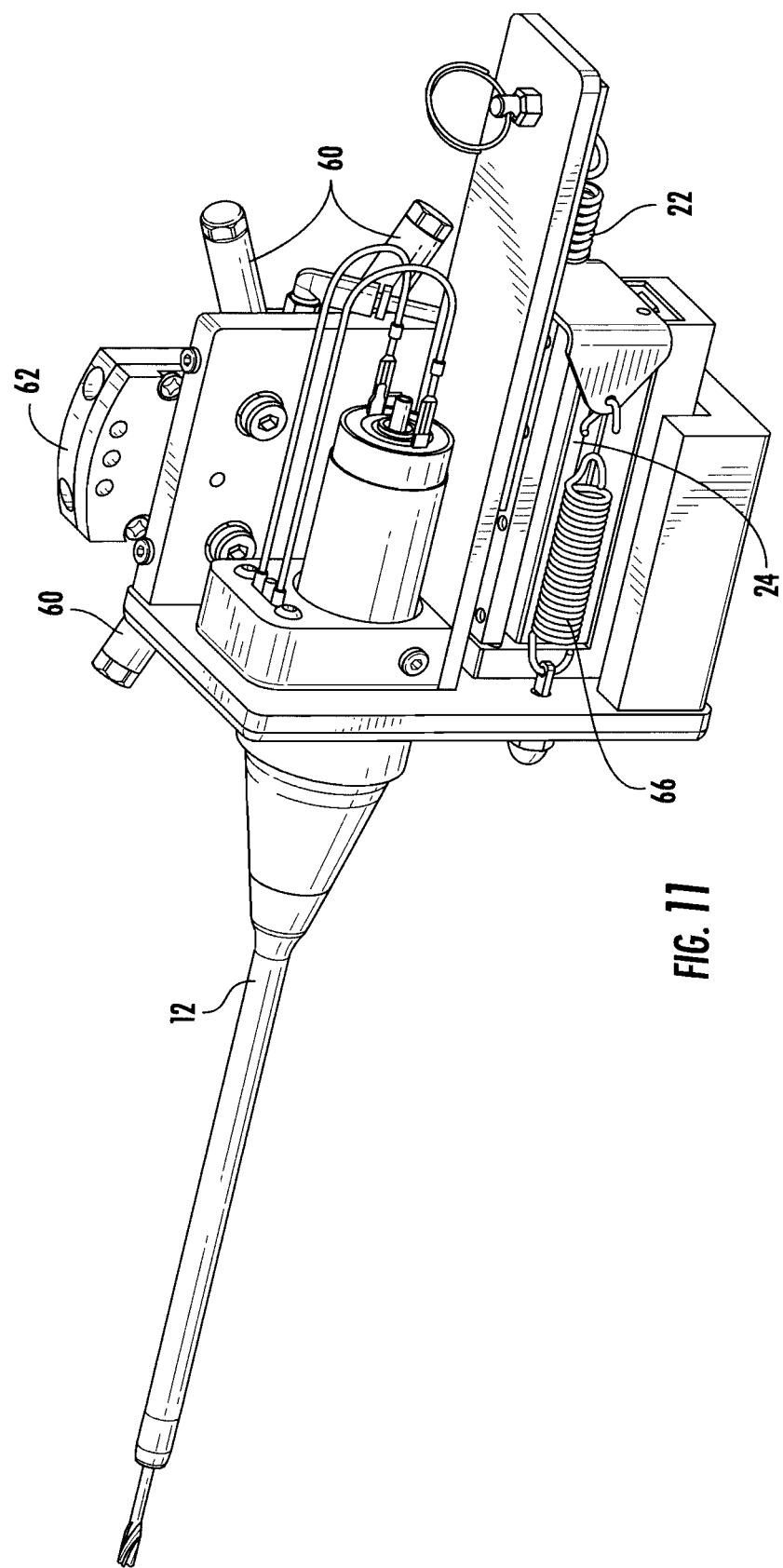
FIG. 11 is a partial perspective view illustrating an alternative embodiment of the present invention.
Figure 12:
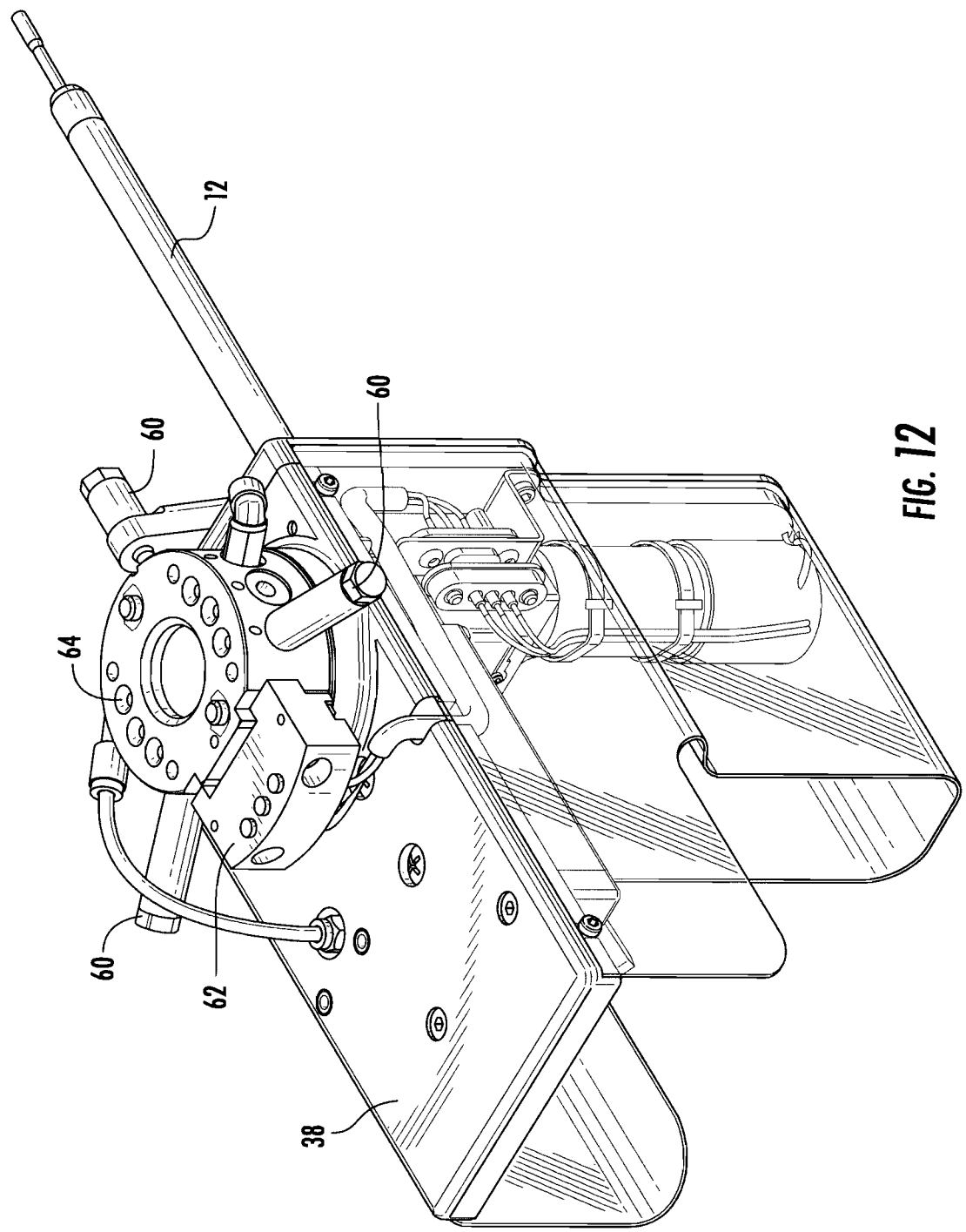
FIG. 12 is a partial perspective view illustrating a quick tool change connector for use with a robot equipped with automatic tool change features.
Figure 13:
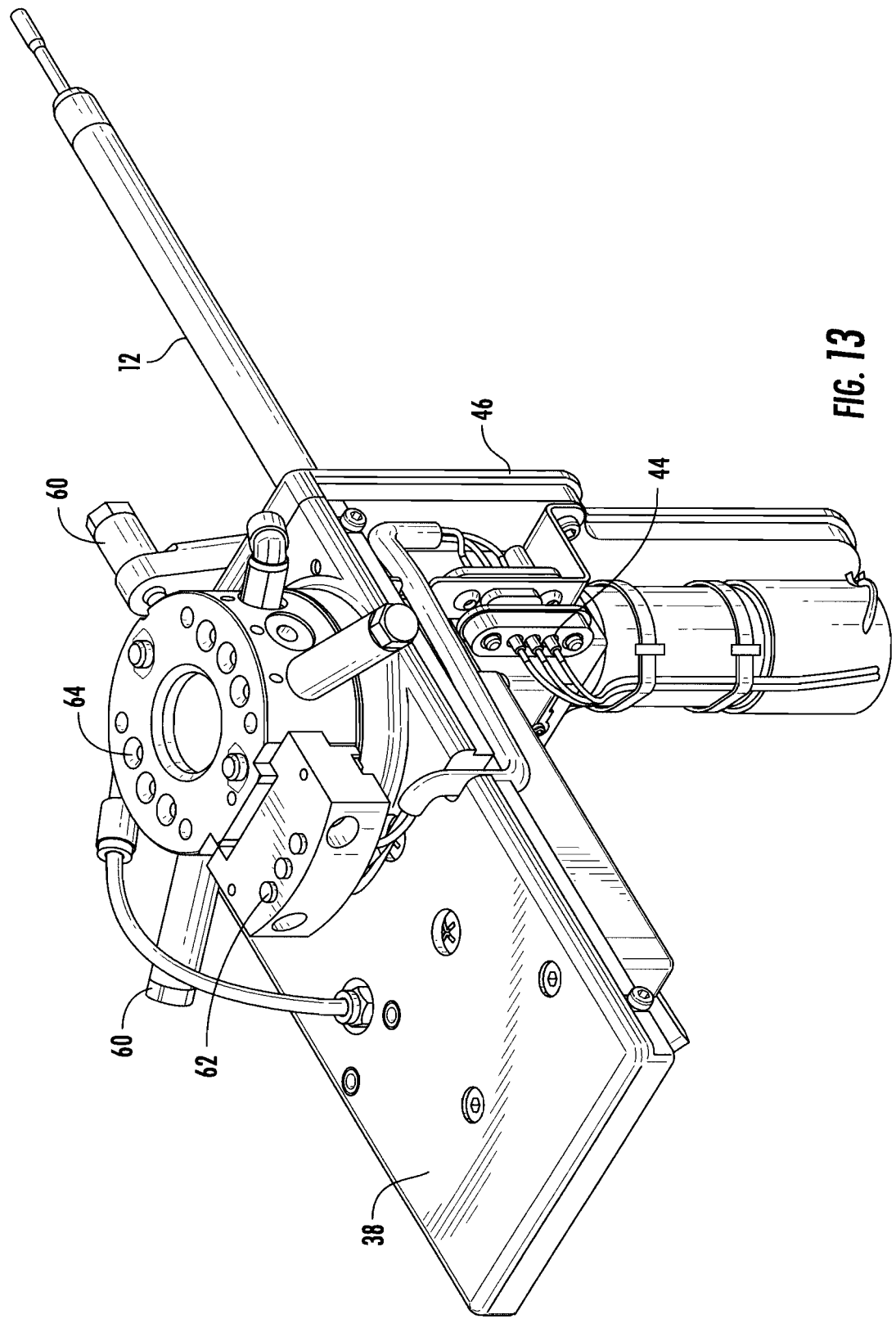
FIG. 13 is a partial perspective view of the embodiment illustrated in FIG. 12.
Figure 14:
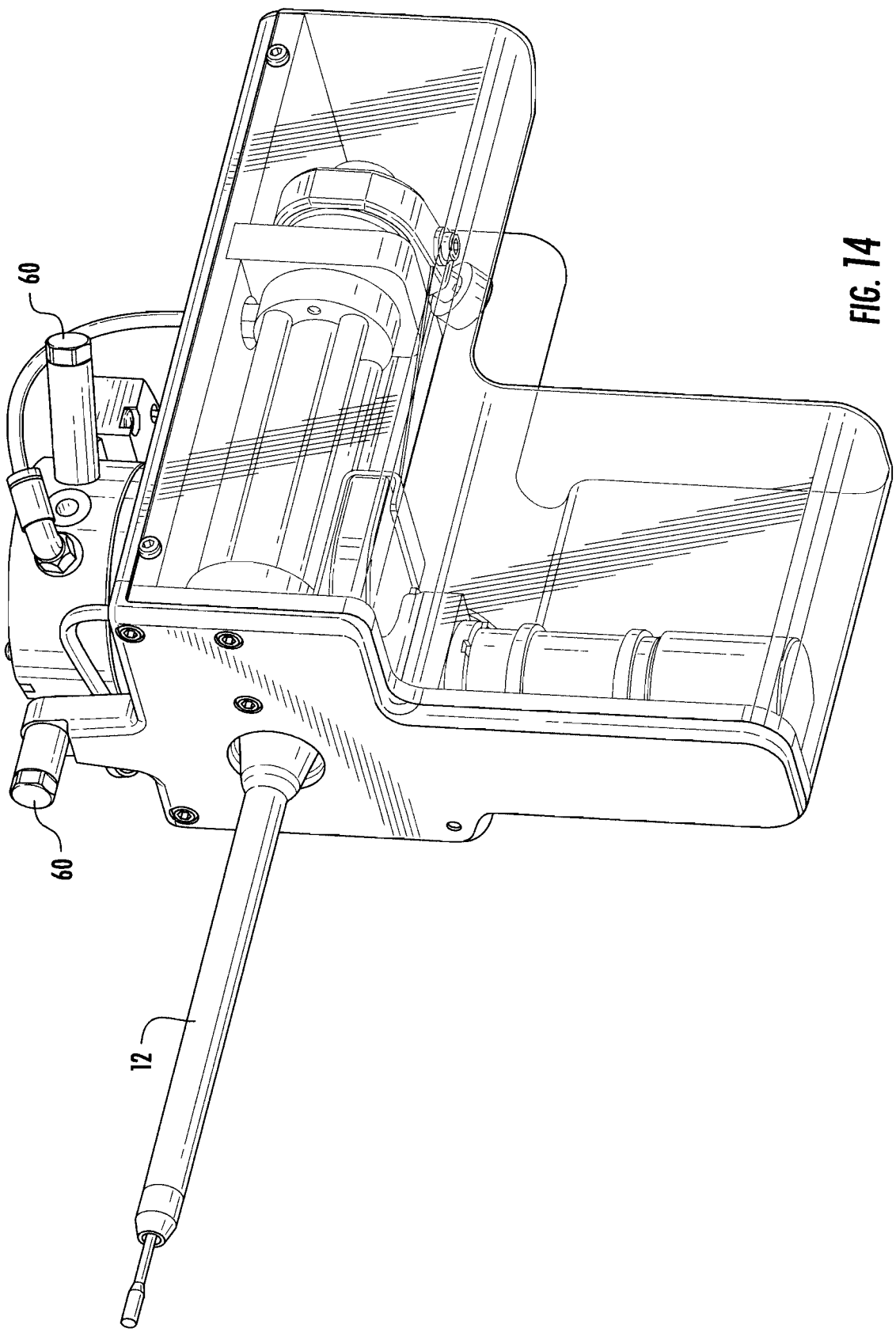
FIG. 14 is a front perspective view of one embodiment illustrated with shields in position.
Figure 15:
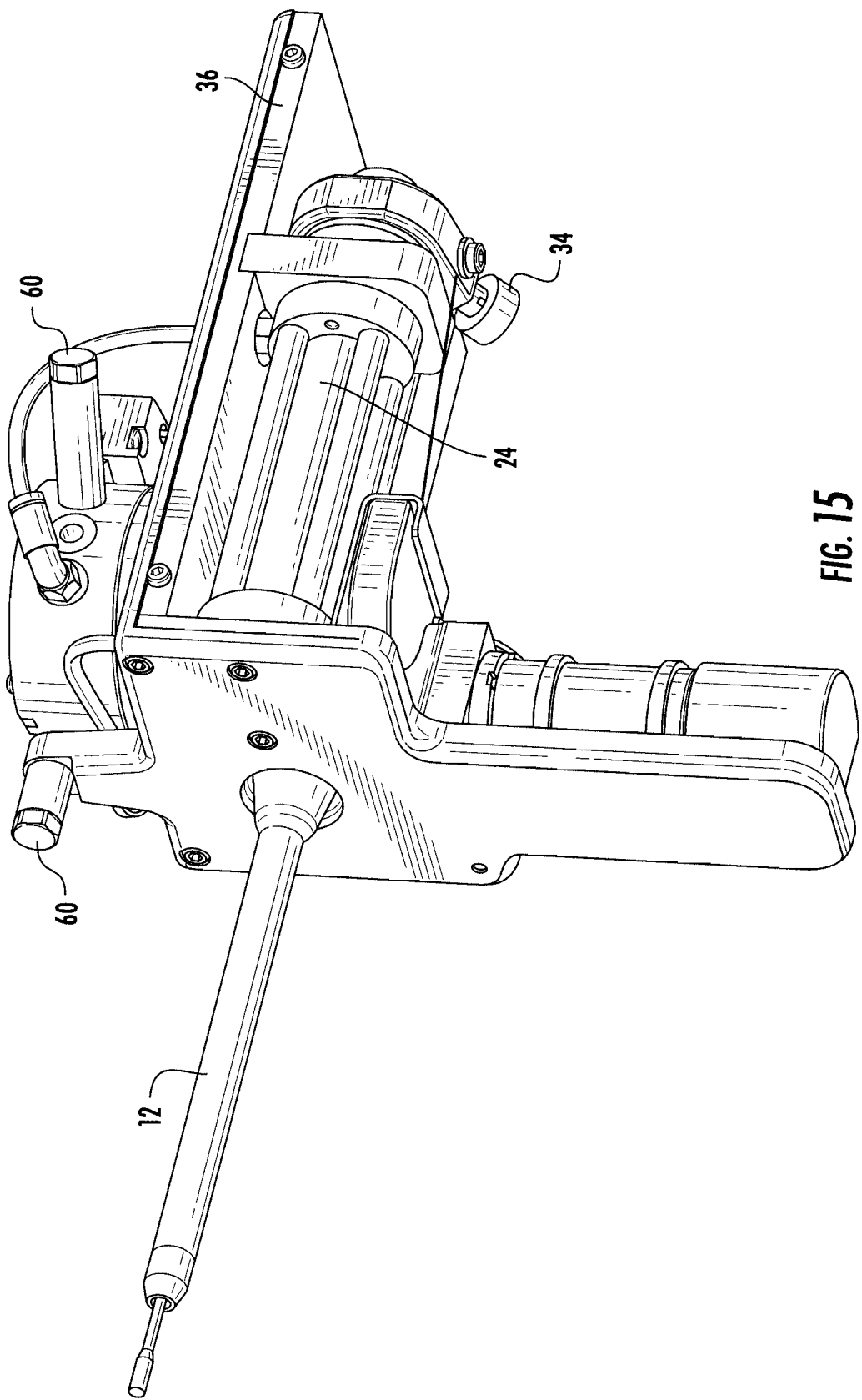
FIG. 15 is a front perspective view of the embodiment shown in FIG. 14 illustrated with shields removed.
Figure 16:
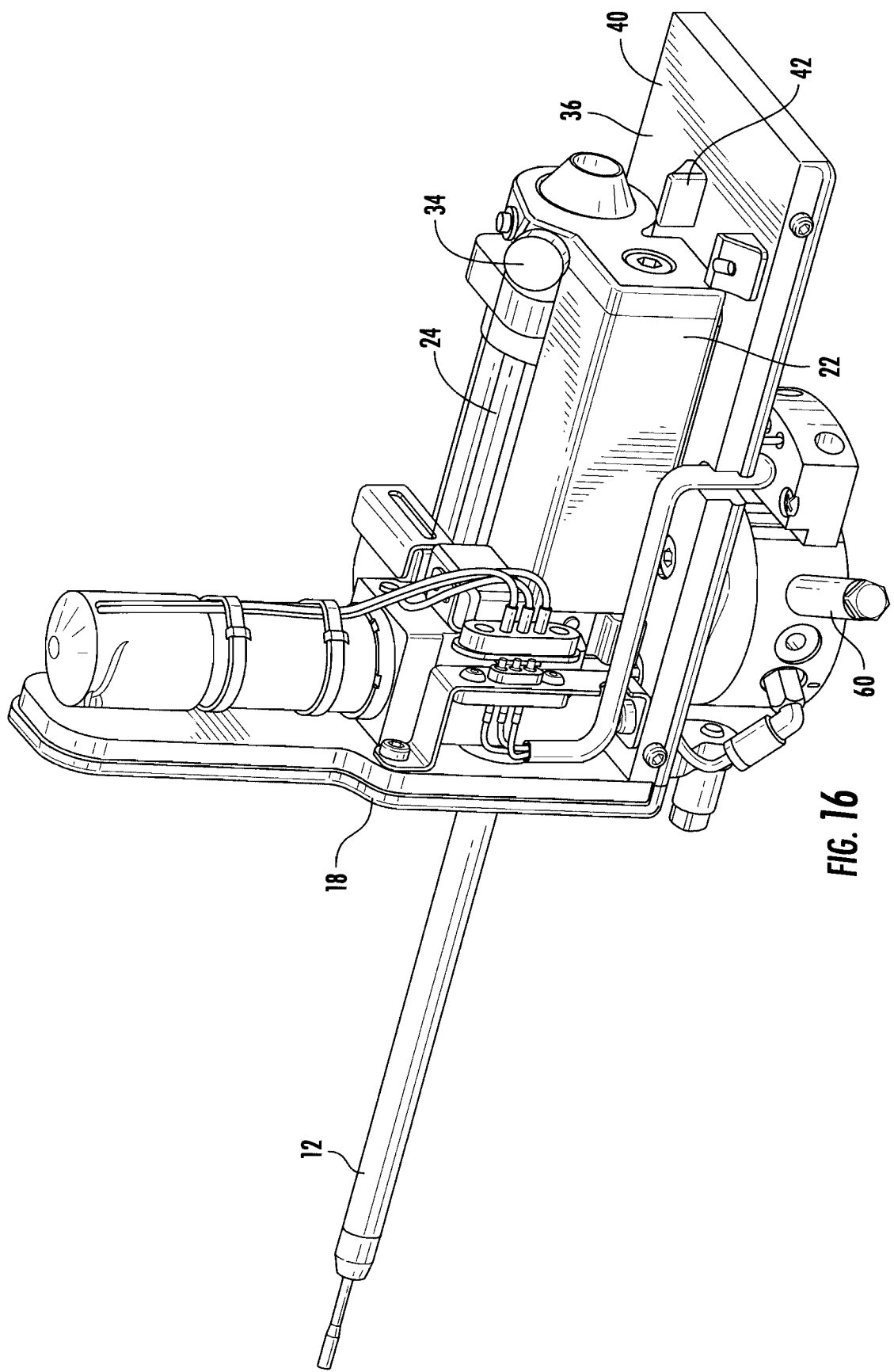
FIG. 16 is a bottom perspective view of the embodiment shown in FIG. 14.
Figure 17:
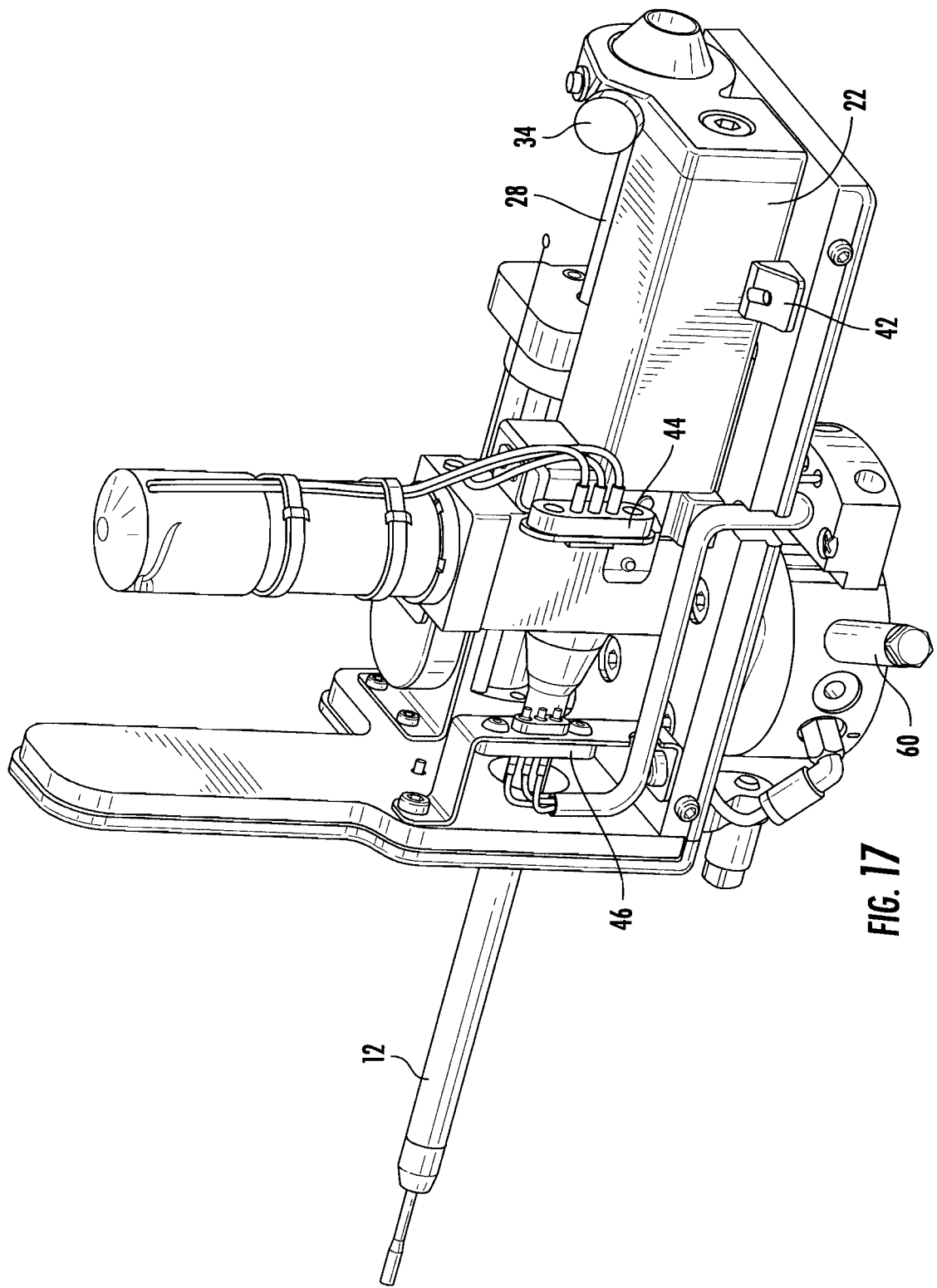
FIG. 17 is a bottom perspective view of the embodiment shown in FIG. 14 illustrated in the retracted position.
Figure 18:
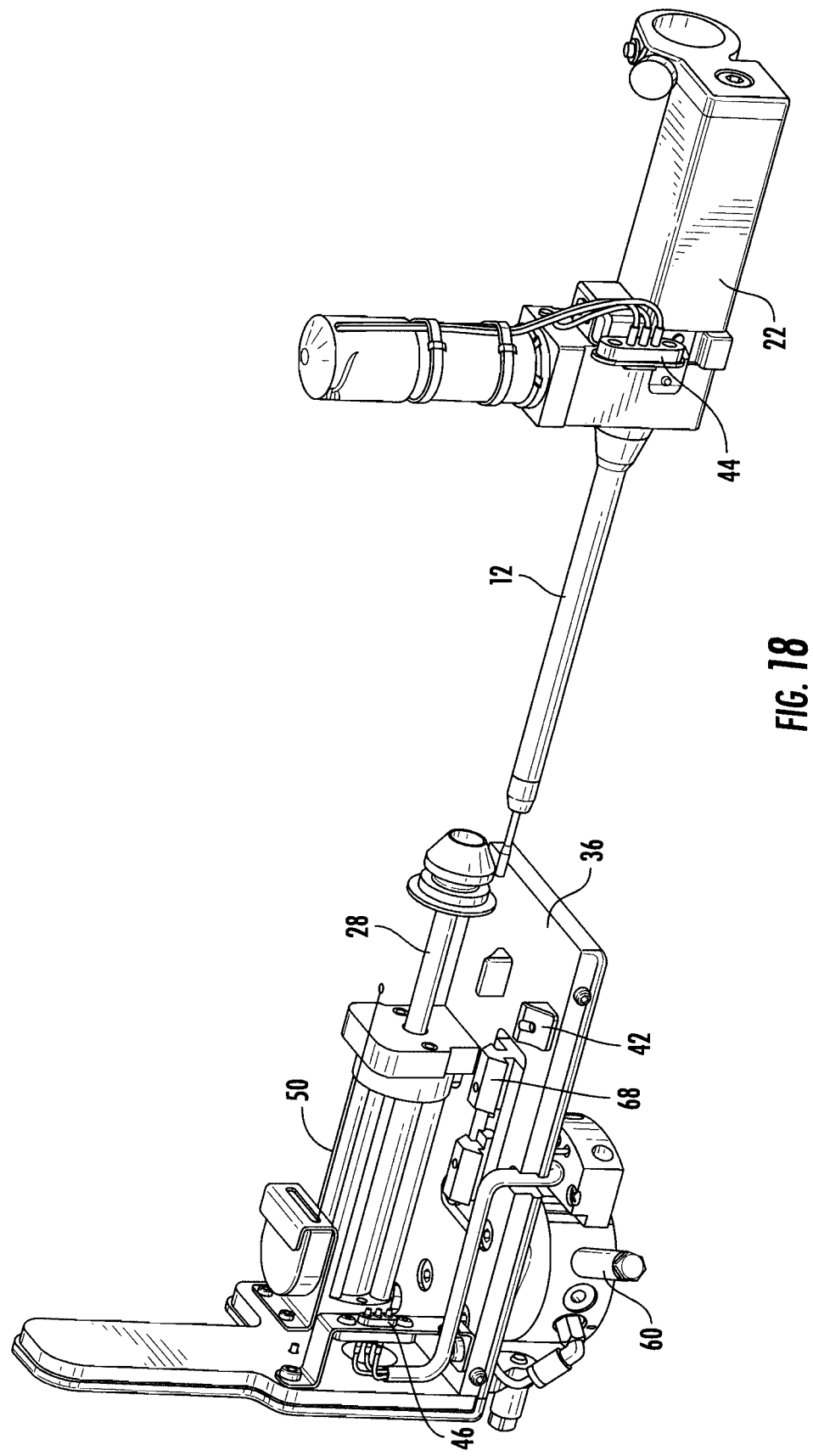
FIG. 18 is a bottom perspective view of the embodiment shown in FIG. 14 illustrated removing the cutting tool.

Referring to FIG. 11, an alternative embodiment of the present device and system is illustrated. In this embodiment, springs 66 are utilized to position the surgical tool 12 in the operational position, while an air cylinder 24 is utilized to move the shuttle 22 to the non-operational position. Removal of the pneumatic motive force allows the surgical tool to automatically reposition itself to the operational position. It should also be noted that this construction allows electrical solenoids and the like to be utilized in place of the air cylinder without departing from the scope of the invention.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

What is claimed is:

1. A system for retracting a surgical tool from a surgical site comprising:
   a robot having an attachment point for securing a surgical tool, the robot configured for robotically controlled movement of the surgical tool; and
   a retraction mechanism for automatically causing said surgical tool to retract from a first operational position to a second non-operational position independent of the robotically controlled movement upon detection of a predetermined condition.

2. The system for retracting a surgical tool from a surgical site of claim 1, wherein said retraction mechanism includes a track portion and a shuttle portion, a functional portion of said surgical tool secured to said shuttle portion to move therewith upon detection of said predetermined condition.

3. The system for retracting a surgical tool from a surgical site of claim 2, wherein movement of said shuttle portion disables the robotically controlled movement of said functional portion of said surgical tool.

4. The system for retracting a surgical tool from a surgical site of claim 3, wherein a motive power is disabled to said functional portion of said surgical tool.

5. The system for retracting a surgical tool from a surgical site of claim 4, wherein movement of said shuttle portion is provided by a second source of motive power.

6. The system for retracting a surgical tool from a surgical site of claim 5, wherein said second source of motive power is pneumatic.

7. The system for retracting a surgical tool from a surgical site of claim 6, wherein said pneumatic motive power is an air cylinder having a moveable piston therein, whereby said pneumatic motive power is supplied to a first side of said moveable piston to position said surgical tool in said first operational position, and whereby supplying said pneumatic motive power to a second side of said piston causes said surgical tool to retract to said second non-operational position.

8. The system for retracting a surgical tool from a surgical site of claim 6, wherein said first side of said piston includes a rod member secured thereto, said rod member extending outside of said air cylinder, said rod moving with said moveable piston, said rod connected to said shuttle portion so that said shuttle portion moves with said moveable piston.

9. The system for retracting a surgical tool from a surgical site of claim 8, wherein said shuttle portion is removably secured to said rod, whereby said surgical tool is removable and replaceable with respect to said shuttle portion.

10. The system for retracting a tool from a surgical site of claim 9, wherein said shuttle portion is removably secured to said rod via a hand operated spring pin.

11. The system for retracting a surgical tool from a surgical site of claim 2, wherein said track portion is secured to said attachment point of said robot to be moveable therewith.

12. The system for retracting a surgical tool from a surgical site of claim 11, wherein said track portion includes a plate, said plate having a first side surface and a second side surface, said first side surface secured to said robot attachment point, said second side surface including said track portion, said track portion including at least two guide members for guiding said shuttle during movement thereof to said non-operational position.

13. The system for retracting a surgical tool from a surgical site of claim 12, wherein said shuttle includes at least one first electrical contact, said track portion including at least one second electrical contact, said at least one first electrical contact and said at least one second electrical contact positioned to contact each other when said shuttle portion is positioned in said first operational position, and thus provide electrical flow to said surgical tool for operation thereof.

14. The system for retracting a surgical tool from a surgical site of claim 13, wherein said at least one first electrical contact and said at least one second electrical contact are separated during movement of said shuttle portion to said second non-operational position, thereby disabling a motive movement of said surgical tool.

15. The system for retracting a surgical tool from a surgical site of claim 12, wherein said first side surface of said plate includes a tool change structure for interlocking cooperation with a tool change mechanism, said tool change mechanism secured to a robot arm to provide for tool interchangeability to said robot, said surgical tool being a self-contained system connectable to said tool change mechanism to provide said first motive power and said second motive power to said surgical tool retraction system.

16. The system for retracting a surgical tool from a surgical site of claim 15, wherein said tool change mechanism includes at least one primary electrical contact for supplying electrical motive power to said tool change structure and thus said surgical tool for operation thereof.

17. The system for retracting a surgical tool from a surgical site of claim 16, wherein said tool change mechanism includes at least one primary pneumatic connection for supplying pneumatic motive power to a cylinder for operation thereof.

18. The system for retracting a surgical tool from a surgical site of claim 15, wherein said tool change structure includes a pilot aperture for providing a positional location of said surgical tool with respect to said robot arm.

19. The system for retracting a surgical tool from a surgical site of claim 18, wherein said tool change structure includes a plurality of rod members secured about said pilot aperture for providing orientation of said surgical tool with respect to said robot arm.

20. The system for retracting a tool from a surgical site of claim 1, wherein said surgical tool includes a first set of electrical contacts for receiving electrical power from a second set of electrical contacts and retraction from the first operational position to the second non-operational position causes the first set of electrical contacts to disconnect from the second set of electrical contacts.

* * * * *